US011591481B2

(12) United States Patent
Mizukami et al.

(10) Patent No.: US 11,591,481 B2
(45) Date of Patent: Feb. 28, 2023

(54) CELLULOSE FIBER-CONTAINING COMPOSITION, PRODUCTION METHOD THEREOF, AND FILM

(71) Applicant: OJI HOLDINGS CORPORATION, Tokyo (JP)

(72) Inventors: Moe Mizukami, Tokyo (JP); Hayato Fushimi, Chiba (JP); Hirokazu Sunagawa, Tokyo (JP)

(73) Assignee: OJI HOLDINGS CORPORATION, Tokyo (JP)

( * ) Notice: Subject to any disclaimer, the term of this patent is extended or adjusted under 35 U.S.C. 154(b) by 290 days.

(21) Appl. No.: 16/633,764

(22) PCT Filed: Jul. 13, 2018

(86) PCT No.: PCT/JP2018/026533
§ 371 (c)(1),
(2) Date: Jan. 24, 2020

(87) PCT Pub. No.: WO2019/021866
PCT Pub. Date: Jan. 31, 2019

(65) Prior Publication Data
US 2021/0122932 A1    Apr. 29, 2021

(30) Foreign Application Priority Data
Jul. 25, 2017    (JP) .............................. JP2017-143397

(51) Int. Cl.
*C09D 7/00* (2018.01)
*C09D 7/43* (2018.01)
(Continued)

(52) U.S. Cl.
CPC ................. *C09D 7/43* (2018.01); *C09D 7/65* (2018.01); *C09D 7/70* (2018.01); *C09D 101/04* (2013.01); *C09D 101/16* (2013.01)

(58) Field of Classification Search
None
See application file for complete search history.

(56) References Cited

U.S. PATENT DOCUMENTS

| | | | |
|---|---|---|---|
| 6,083,581 A | 7/2000 | Lacoste-Bourgeacq et al. | |
| 6,495,190 B1 * | 12/2002 | Yaginuma | C08L 5/00 426/573 |

(Continued)

FOREIGN PATENT DOCUMENTS

| | | | |
|---|---|---|---|
| CN | 105926063 A * | 9/2016 | ............. D01F 11/02 |
| EP | 2 853 635 A1 | 4/2015 | |

(Continued)

OTHER PUBLICATIONS

Pesaran et al, Effect of cultivation time and medium condition in production of bacterial cellulose nanofiber for urease immobilization, international journal of polymer science, 15, pp. 1-8 (Year: 2015).*

(Continued)

*Primary Examiner* — Stefanie J Cohen
(74) *Attorney, Agent, or Firm* — Sughrue Mion, PLLC

(57) ABSTRACT

It is an object of the present invention to provide a cellulose-containing composition having excellent coating suitability, a production method thereof, and a film. According to the present invention, provided is a cellulose-containing composition comprising cellulose fibers having a fiber width of 1000 nm or less and protein, wherein the protein includes an enzyme, the content of the protein is $1 \times 10^{-3}$ parts by mass or less with respect to 1 part by mass of the cellulose fibers, and when the cellulose-containing composition having a solid concentration of 0.4% by mass is obtained, the viscosity of the cellulose-containing composition measured under conditions of 25° C. and a rotation number of 3 rpm is 10 mPa·s or more and 11000 mPa·s or less.

4 Claims, 2 Drawing Sheets

(51) Int. Cl.
*C09D 7/65* (2018.01)
*C09D 7/40* (2018.01)
*C09D 101/04* (2006.01)
*C09D 101/16* (2006.01)

(56) References Cited

U.S. PATENT DOCUMENTS

| | | | |
|---|---|---|---|
| 2007/0006774 | A1 | 1/2007 | Rogers et al. |
| 2009/0085008 | A1* | 4/2009 | Tanaka ................ C08L 1/12 560/60 |
| 2010/0022437 | A1* | 1/2010 | Artiga-Gonzalez ... C11D 3/221 424/490 |
| 2011/0286948 | A1* | 11/2011 | Lin ...................... A61P 17/00 424/94.1 |
| 2015/0368541 | A1* | 12/2015 | Monclin ............... C09K 8/887 507/108 |
| 2016/0090564 | A1* | 3/2016 | Loughnane ........... C11D 1/88 510/320 |
| 2016/0115249 | A1 | 4/2016 | Noguchi et al. |
| 2016/0194462 | A1* | 7/2016 | Wada .................... C08B 15/00 428/401 |

FOREIGN PATENT DOCUMENTS

| | | |
|---|---|---|
| EP | 3 677 653 A1 | 7/2020 |
| JP | 2008-075214 A | 4/2008 |
| JP | 2008-150719 A | 7/2008 |
| JP | 2009-298972 A | 12/2009 |
| JP | 2013-163773 A | 8/2013 |
| JP | 2014-101604 A | 6/2014 |
| JP | 2014-125689 A | 7/2014 |
| JP | 2015-221844 A | 12/2015 |
| JP | 2017-002136 A | 1/2017 |
| JP | 2017-66272 A | 4/2017 |
| JP | 2017-125279 A | 7/2017 |
| WO | 2011/118748 A1 | 9/2011 |

OTHER PUBLICATIONS

CN-105926063-A, English translation (Year: 2016).*
Gourlay Keith et al., "The Potential of endoglucanases to rapidly and specifically enhance the rheological properties of micro/nanofibrillated cellulose", Cellulose, Springer Netherlands, Netherlands, vol. 25, No. 2, Dec. 29, 2017, pp. 977-986 (10 pages total).
Wang Wangxia et al., "Endoglucanase post-milling treatment for producing cellulose nanofibers from bleached eucalyptus fibers by a supermasscolloider", Cellulose, Springer Netherlands, Netherlands, vol. 23, No. 3, Apr. 27, 2016, pp. 1859-1870 (12 pages total).
Extended European Search Report dated Feb. 24, 2021 from the European Patent Office in EP Application No. 18837188.4.
International Search Report and Written Opinion dated Aug. 14, 2018, in International Application No. PCT/JP2018/026533.
International Preliminary Report on Patentability with translation of the Written Opinion dated Jan. 28, 2020, in International Application No. PCT/JP2018/026533.
Decision of Refusal dated Aug. 7, 2018, from the Japanese Patent Office in application No. 2017-143397.
Office Action dated Apr. 10, 2018, from the Japanese Patent Office in application No. 2017-143397.
Office Action dated Dec. 19, 2017, from the Japanese Patent Office in application No. 2017-143397.
Office Action dated Jul. 27, 2022 by European Patent Office in European Application No. 18837188.4.
Office Action dated Nov. 3, 2022 by the Chinese Patent Office in Chinese Application No. 201880049664.3.

* cited by examiner

[Figure 1]
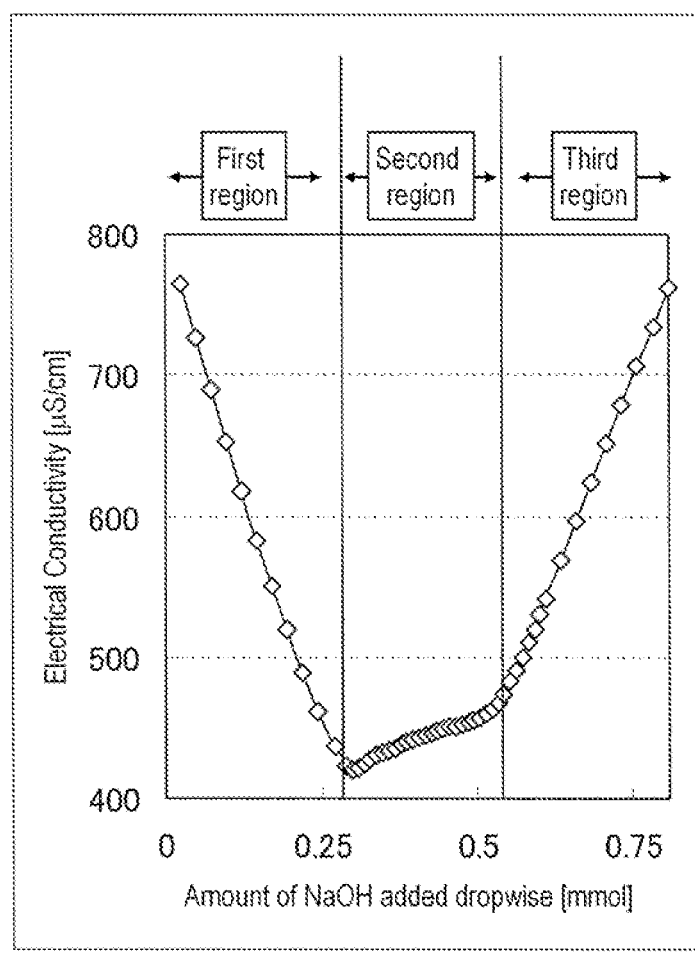

[Figure 2]
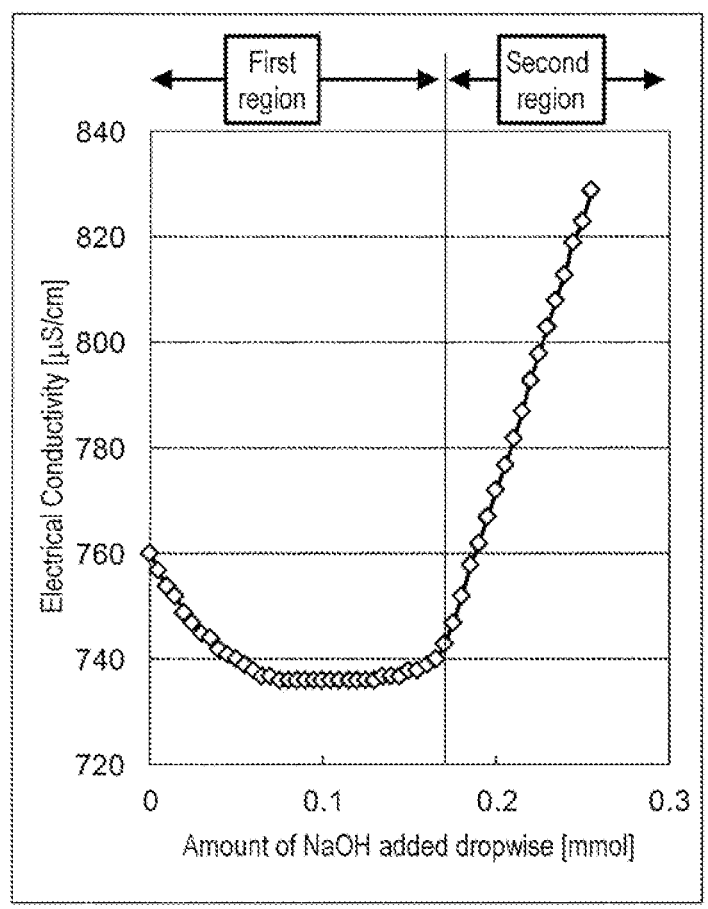

CELLULOSE FIBER-CONTAINING COMPOSITION, PRODUCTION METHOD THEREOF, AND FILM

CROSS REFERENCE TO RELATED APPLICATIONS

This application is a National Stage of International Application No. PCT/JP2018/026533 filed Jul. 13, 2018, claiming priority based on Japanese Patent Application No. 2017-143397 filed Jul. 25, 2017.

TECHNICAL FIELD

The present invention relates to an ultrafine cellulose fiber-containing composition, a production method thereof, and a film.

BACKGROUND ART

In recent years, because of enhanced awareness of alternatives to petroleum resources and environmental consciousness, there has been a focus on materials utilizing reproducible natural fibers. Among natural fibers, cellulose fibers having a fiber diameter of 10 μm or more and 50 μm or less, in particular, wood-derived cellulose fibers (pulp) have been widely used mainly as paper products so far.

Ultrafine cellulose fibers, which have a fiber diameter of 1 μm or less, have also been known as cellulose fibers. In recent years, a sheet composed of such ultrafine cellulose fibers, and a composite sheet comprising an ultrafine cellulose fiber-containing sheet and a resin, have been developed. Since ultrafine cellulose fibers can exhibit thickening action, the use of such ultrafine cellulose fibers as a thickener for various intended uses has also been studied.

As a method for producing a dispersed form of ultrafine cellulose fibers, Patent Document 1 discloses that chemically modified cellulose fibers are defibrated to obtain a cellulose nanofiber-dispersed form. Patent Document 1 describes that enzymatically treated cellulose fibers may be used as chemically modified cellulose fibers. In addition, Patent Document 2 discloses that oxidized cellulose is fibrillated in an aqueous medium to obtain a dispersed solution of ultrafine cellulose fibers. Patent Document 2 describes that a cellulose raw material may be enzymatically treated.

PRIOR ART DOCUMENTS

Patent Documents

Patent Document 1: JP-A-2017-2136
Patent Document 2: JP-A-2015-221844

SUMMARY OF INVENTION

Object to be Solved by the Invention

For the purpose of reinforcing a paint, the present inventors have studied the use of ultrafine cellulose fibers. However, since such ultrafine cellulose fibers have high viscosity, for intended use that does not desire viscosity increase, it has been difficult to add ultrafine cellulose fibers in an amount sufficient to reinforce a paint. For example, when a coating film is formed with a paint, ultrafine cellulose fibers having low viscosity are excellent in terms of coating suitability. It is an object of the present invention to provide a cellulose-containing composition having excellent coating suitability, a production method thereof, and a film.

Means for Solving the Object

As a result of intensive studies directed towards achieving the aforementioned object, the present inventors have found that the viscosity of a composition containing cellulose fibers having a fiber width of 1000 nm or less is adjusted by addition of an enzyme, so that a cellulose-containing composition having excellent coating suitability can be obtained. The present invention has been completed based on these findings.

The present invention has the following configurations.

[1] A cellulose-containing composition comprising cellulose fibers having a fiber width of 1000 nm or less and protein, wherein the protein includes an enzyme, the content of the protein is $1 \times 10^{-3}$ parts by mass or less with respect to 1 part by mass of the cellulose fibers, and when the cellulose-containing composition having a solid concentration of 0.4% by mass is obtained, the viscosity of the cellulose-containing composition measured under conditions of 25° C. and a rotation number of 3 rpm is 10 mPa·s or more and 11000 mPa·s or less.

[2] The cellulose-containing composition according to [1], wherein the content of the protein is $1 \times 10^{-7}$ parts by mass or more with respect to 1 part by mass of the cellulose fibers.

[3] A cellulose-containing composition comprising cellulose fibers having a fiber width of 1000 nm or less and protein, wherein the protein includes an enzyme, the endoglucanase activity of the enzyme is 840 U/L or less, and when the cellulose-containing composition having a solid concentration of 0.4% by mass is obtained, the viscosity of the cellulose-containing composition measured under conditions of 25° C. and a rotation number of 3 rpm is 10 mPa·s or more and 11000 mPa·s or less.

[4] The cellulose-containing composition according to [3], wherein the endoglucanase activity of the enzyme is 0.084 U/L or more.

[5] The cellulose-containing composition according to any one of [1] to [4], wherein the cellulose fibers have ionic substituents.

[6] The cellulose-containing composition according to any one of [1] to [5], wherein the cellulose fibers have phosphoric acid groups or phosphoric acid group-derived substituents.

[7] The cellulose-containing composition according to any one of [1] to [6], wherein the polymerization degree of the cellulose fibers is 200 or more and 450 or less.

[8] A film comprising cellulose fibers having a fiber width of 1000 nm or less and protein, wherein the protein includes an enzyme, and the content of the protein is $1 \times 10^{-3}$ parts by mass or less with respect to 1 part by mass of the cellulose fibers.

[9] The film according to [8], wherein the content of the protein is $1 \times 10^{-7}$ parts by mass or more with respect to 1 part by mass of the cellulose fibers.

[10] A method for producing a cellulose-containing composition, comprising adding an enzyme in an amount of $1 \times 10^{-3}$ parts by mass or less with respect to 1 part by mass of cellulose fibers having a fiber width of 1000 nm or less.

Advantageous Effects of Invention

According to the present invention, a cellulose-containing composition having excellent coating suitability can be provided.

BRIEF DESCRIPTION OF DRAWINGS

FIG. 1 is a graph showing the relationship between the amount of NaOH added dropwise to a fiber raw material having a phosphoric acid group and the electrical conductivity.

FIG. 2 is a graph showing the relationship between the amount of NaOH added dropwise to a fiber raw material having a carboxyl group and the electrical conductivity.

EMBODIMENTS OF CARRYING OUT THE INVENTION

Hereinafter, the present invention will be described in detail. The description for components described below will be based on representative embodiments or specific examples; however, the present invention will not be limited to such embodiments.
(Cellulose-Containing Composition)

The present invention relates to a cellulose-containing composition comprising cellulose fibers having a fiber width of 1000 nm or less (hereinafter also referred to as "ultrafine cellulose fibers") and protein, wherein the protein includes an enzyme, the content of the protein is $1 \times 10^3$ parts by mass or less with respect to 1 part by mass of the cellulose fibers, and when the cellulose-containing composition having a solid concentration of 0.4% by mass is obtained, the viscosity of the cellulose-containing composition measured under conditions of 25° C. and a rotation number of 3 rpm is 10 mPa·s or more and 11000 mPa·s or less.

The content of the protein may be $1 \times 10^{-3}$ parts by mass or less with respect to 1 part by mass of the cellulose fibers, and it is preferably $1 \times 10^{-4}$ parts by mass or less, more preferably $1 \times 10^{-5}$ parts by mass or less, and particularly preferably $5.0 \times 10^{-6}$ parts by mass or less. On the other hand, the content of the protein is preferably $1 \times 10^{-7}$ parts by mass or more, more preferably $3 \times 10^{-7}$ parts by mass or more, and further preferably $1 \times 10^{-6}$ parts by mass or more, with respect to 1 part by mass of the cellulose fibers.

The content of the protein can be regulated, for example, by adjusting the amount of an enzyme added, or by adjusting a process of producing ultrafine cellulose fibers, including an enzyme treatment. In the present embodiment, the amount of the protein can be adjusted, for example, by utilizing the timing of performing an enzyme treatment. By setting the content of the protein within the above-described range, favorable coating suitability can be achieved.

The content of the protein in the cellulose-containing composition can be obtained, for example, by a burette method, a Lowry's method, a fluorescence method, or a dye-binding method. When the content of the protein is obtained by such a burette method, a burette reagent is added to a bovine serum albumin aqueous solution (which is an aqueous solution having protein amount of 5.0% by mass or less) in an amount that is 4 times larger than the amount of the bovine serum albumin aqueous solution, followed by blending. The thus obtained mixture is left under the environment of 20° C. to 25° C. for 30 minutes, and the absorption wavelength at 540 nm is then measured using a spectrophotometer. Based on the measured value, a calibration curve is drawn. Subsequently, a burette reagent is added to the cellulose-containing composition in an amount that is 4 times larger than the amount of the cellulose-containing composition, followed by fully blending. The thus obtained mixture is left under the environment of 20° C. to 25° C. for 30 minutes, and the absorption wavelength at 540 nm is then measured using a spectrophotometer. The measured value is written in the calibration curve, so that the amount of the protein contained in the cellulose-containing composition can be obtained.

Moreover, the present invention relates to a cellulose-containing composition comprising cellulose fibers having a fiber width of 1000 nm or less and protein, wherein the protein includes an enzyme, the endoglucanase activity of the enzyme is 840 U/L or less, and when the cellulose-containing composition having a solid concentration of 0.4% by mass is obtained, the viscosity of the cellulose-containing composition measured under conditions of 25° C. and a rotation number of 3 rpm is 10 mPa·s or more and 11000 mPa·s or less.

The endoglucanase activity of the enzyme may be 840 U/L or less. The lower limit of the endoglucanase activity of the enzyme is preferably 0.084 U/L or more, more preferably 0.84 U/L or more, even more preferably 1 U/L or more, further preferably 2 U/L or more, and particularly preferably 3 U/L or more. The upper limit of the endoglucanase activity of the enzyme is preferably 84 U/L or less, more preferably 8.4 U/L or less, further preferably 7 U/L or less, and particularly preferably 6 U/L or less.

The endoglucanase activity of the enzyme can be regulated, for example, by adjusting the amount of an enzyme added, or by adjusting a process of producing ultrafine cellulose fibers, including an enzyme treatment. In the present embodiment, the endoglucanase activity of the enzyme can be adjusted, for example, by utilizing the timing of performing an enzyme treatment. By setting the endoglucanase activity of the enzyme within the above-described range, favorable coating suitability can be achieved The endoglucanase activity of the enzyme (also referred to as "EG activity") in the cellulose-containing composition can be measured as follows.

A substrate solution of 1% (W/V) carboxymethyl cellulose (concentration: 100 mM; containing an acetic acid-sodium acetate buffer with pH 5.0) is prepared. The cellulose-containing composition immediately after the production thereof has previously been diluted with a buffer (the same as described above) (wherein the dilution rate is set, so that the absorbance of the following enzyme solution can be in the calibration curve obtained from the following glucose standard solution). Then, 10 μl of the thus diluted slurry solution to be evaluated is added to 90 μl of the substrate solution, and a reaction is then carried out at 37° C. for 30 minutes. In order to prepare a calibration curve, ion exchange water (blank) and glucose standard solutions (at least, 4 standard solutions each having a different concentration selected from a concentration of 0.5 to 5.6 mM) are selected, and these solutions are prepared in an amount of 100 μl each. The thus prepared solutions are incubated at 37° C. for 30 minutes. After completion of the reaction, to each of the enzyme-containing slurry solution to be evaluated, the blank for the calibration curve, and the glucose standard solutions, 300 μl of DNS coloring solution (1.6% by mass of NaOH, 1% by mass of 3,5-dinitrosalicylic acid, and 30% by mass of potassium sodium tartrate) is added, and each mixed solution is boiled for 5 minutes for color development. Immediately after the color development, the reaction mixture is cooled on ice, and 2 ml of ion exchange water is then added thereto, followed by fully blending. The reaction mixture is left at rest for 30 minutes, and then, absorbance is measured within 1 hour. Regarding the measurement of the absorbance, 200 μl of the reaction mixture is dispensed in a 96-well microwell plate, and the absorbance at 540 nm is then measured using a microplate reader. Using the absorbance of each glucose standard solution, from which the absorbance of the blank is subtracted, and the glucose concentration, a calibration curve is produced. The amount of corresponding glucose generated in the cellulose-containing composition is calculated using the calibration curve, after subtracting the absorbance of the blank from the absorbance of the cellulose-containing composition. The amount of an enzyme that generates reducing sugar equivalent to 1 μmol of glucose for 1 minute is defined as 1 unit, and EG activity is obtained according to the following equation:

EG activity=Amount (μmol) of corresponding glucose generated in 1 ml of cellulose-containing composition obtained by dilution with buffer/30 minutes×dilution rate The viscosity of the cellulose-containing composition of the present invention having a solid concentration of 0.4% by mass, which is measured under conditions of 25° C. and a rotation number of 3 rpm, is 10 mPa·s or more and 11000 mPa·s or less. The lower limit of the viscosity is preferably 100 mPa·s or more, more preferably 200 mPa·s or more, further preferably 500 mPa·s or more, and particularly preferably 1000 mPa·s or more. The upper limit of the viscosity is preferably 10000 mPa·s or less, more preferably 8000 mPa·s or less, even more preferably 6500 mPa·s or less, further preferably 5000 mPa·s or less, still further preferably 4000 mPa·s or less, particularly preferably 3000 mPa·s or less, and most preferably 2000 mPa·s or less.

The above-described viscosity is measured by pouring ion exchange water onto a cellulose-containing composition 24 hours after the production thereof, so as to prepare a diluted solution having a solid concentration of 0.4% by mass, then leaving the diluted solution at rest under the environment of 25° C. for 24 hours, and then rotating the resulting solution using a Type B Viscometer (No. 3 Rotor or No. 2 Rotor, or No. 1 Rotor) (manufactured by BROOKFIELD, analog viscometer T-LVT) at 25° C. at a rotation number of 3 rpm for 3 minutes.

Since the cellulose-containing composition of the present invention has the above-described configuration, its coating suitability is improved. In the present invention, an enzyme is added to the ultrafine cellulose fibers after completion of the defibration, so that the viscosity of the ultrafine cellulose fibers can be efficiently adjusted without relying on a mechanical treatment, and thereby, coating suitability can be improved. In addition, since an efficient reduction in viscosity can be realized by adding an enzyme to the ultrafine cellulose fibers after completion of the defibration, the amount of the enzyme added can be reduced. When a film is produced using the cellulose-containing composition of the present invention, the produced film can have favorable optical properties and mechanical properties according to the above-described effects. It is assumed that this is because deterioration in physical properties can be suppressed by crystallization of enzyme-derived proteins, when a large amount of enzyme is added.

The shape of the cellulose-containing composition is not particularly limited. The cellulose-containing composition can be present in various shapes such as, for example, powders, a slurry, or a solid. Among others, the cellulose-containing composition is preferably a slurry.

(Cellulose Fibers)

The cellulose-containing composition of the present invention comprises cellulose fibers having a fiber width of 1000 nm or less (also referred to as "ultrafine cellulose fibers"). As such cellulose fibers having a fiber width of 1000 nm or less, needle leaf tree-derived cellulose fibers having a fiber width of 1000 nm or less can be preferably used. The ultrafine cellulose fibers preferably have ionic substituents, and in this case, the ionic substituents are preferably anionic substituents (hereinafter also referred to as "anionic groups"). The anionic group is preferably at least one selected from, for example, a phosphoric acid group or a phosphoric acid group-derived substituent (which is simply referred to as a "phosphoric acid group" at times), a carboxyl group or a carboxyl group-derived substituent (which is simply referred to as a "carboxyl group" at times), and a sulfone group or a sulfone group-derived substituent (which is simply referred to as a "sulfone group" at times). The anionic group is more preferably at least one selected from a phosphoric acid group and a carboxyl group; and is particularly preferably a phosphoric acid group.

The content of the ultrafine cellulose fibers is preferably 0.5% by mass or more, more preferably 5% by mass or more, even more preferably 20% by mass or more, further preferably 40% by mass or more, still further preferably 50% by mass or more, and most preferably 55% by mass or more, with respect to the total solid content of the cellulose-containing composition. On the other hand, the content of the ultrafine cellulose fibers is preferably 95% by mass or less.

Although there is no particular restriction on a cellulose fiber raw material for obtaining ultrafine cellulose fibers, pulp is preferably used from the viewpoint of availability and inexpensiveness. Examples of the pulp may include wood pulp, non-wood pulp, and deinked pulp. Examples of the wood pulp may include chemical pulps such as leaf bleached kraft pulp (LBKP), needle bleached kraft pulp (NBKP), sulfite pulp (SP), dissolving pulp (DP), soda pulp (AP), unbleached kraft pulp (UKP), and oxygen bleached kraft pulp (OKP). Further, included are, but not particularly limited to, semichemical pulps such as semi-chemical pulp (SCP) and chemi-ground wood pulp (CGP); and mechanical pulps such as ground pulp (GP) and thermomechanical pulp (TMP, BCTMP). Examples of the non-wood pulp may include, but not particularly limited to, cotton pulps such as cotton linter and cotton lint; non-wood type pulps such as hemp, wheat straw, and bagasse; and cellulose isolated from ascidian, seaweed, etc., chitin, and chitosan. As a deinked pulp, there is deinked pulp using waste paper as a raw material, but it is not particularly limited thereto. The pulp of the present embodiment may be used singly, or in combination of two or more types. Among the above-listed pulp types, wood pulp and deinked pulp including cellulose are preferable from the viewpoint of easy availability. Among wood pulps, chemical pulp is preferable because it has a higher cellulose content to enhance the yield of ultrafine cellulose fibers and decomposition of cellulose in the pulp is mild at the time of fibrillation (defibration) to yield ultrafine cellulose fibers having a long fiber length with a high aspect ratio. Among them, kraft pulp and sulfite pulp are most preferably selected. A film containing the ultrafine cellulose fibers having a long fiber length with a high aspect ratio tends to exhibit a high strength.

The average fiber width of ultrafine cellulose fibers is 1000 nm or less as observed with an electron microscope. The average fiber width is preferably 2 nm or more and 1000 nm or less, more preferably 2 nm or more and less than 1000 nm, even more preferably 2 nm or more and 100 nm or less, further preferably 2 nm or more and 50 nm or less, and still further preferably 2 nm or more and 10 nm or less, but is not particularly limited thereto. When the average fiber width of ultrafine cellulose fibers is less than 2 nm, since they are dissolved in water as cellulose molecules, there appears tendency that the physical properties (strength, rigidity, and dimensional stability) as an ultrafine cellulose fiber are not expressed sufficiently. The ultrafine cellulose fiber is, for example, monofilament cellulose having a fiber width of 1000 nm or less.

The measurement of a fiber width of an ultrafine cellulose fiber by electron microscopic observation is carried out as follows. An aqueous suspension of the ultrafine cellulose fibers having a concentration of 0.05% by mass or more and 0.1% by mass or less is prepared, and the suspension is casted onto a hydrophilized carbon film-coated grid as a sample for TEM observation. If the sample contains wide fibers, SEM images of the surface of the suspension casted onto glass may be observed. The sample is observed using electron microscope images taken at a magnification of 1000×, 5000×, 10000×, or 50000× according to the widths of the constituent fibers. However, the sample, the observation conditions, and the magnification are adjusted so as to satisfy the following conditions:

(1) A single straight line X is drawn in any given portion in an observation image, and 20 or more fibers intersect with the straight line X.

(2) A straight line Y, which intersects perpendicularly with the aforementioned straight line in the same image as described above, is drawn, and 20 or more fibers intersect with the straight line Y.

The widths of the fibers intersecting the straight line X and the straight line Y in the observation image meeting the above-described conditions are visually read. 3 or more sets of images of surface portions, which are at least not overlapped, are thus observed, and the widths of the fibers intersecting the straight line X and the straight line Y are read in the each image. At least 120 fiber widths (20 fibers×2×3=120) are thus read. The average fiber width (which is simply referred to as a "fiber width" at times) of ultrafine cellulose fibers is an average value of the fiber widths thus read.

The fiber length of the ultrafine cellulose fibers is not particularly limited, and it is preferably 0.1 µm or more and 1000 m or less, more preferably 0.1 µm or more and 800 µm or less, and particularly preferably 0.1 µm or more and 600 µm or less. By setting the fiber length within the above-described range, destruction of the crystalline region of the ultrafine cellulose fibers can be suppressed, and the slurry viscosity of the ultrafine cellulose fibers can also be set within an appropriate range. It is to be noted that the fiber length of the ultrafine cellulose fibers can be obtained by an image analysis using TEM, SEM or AFM.

The ultrafine cellulose fibers preferably have a type I crystal structure. In this regard, the fact that the ultrafine cellulose fibers have a type I crystal structure may be identified by a diffraction profile obtained from a wide angle X-ray diffraction photograph using CuKα (λ=1.5418 Å) monochromatized with graphite. Specifically, it may be identified based on the fact that there are typical peaks at two positions near 2θ=14° or more and 17° or less, and near 2θ=22° or more and 23° or less.

The percentage of the type I crystal structure occupied in the ultrafine cellulose fibers is preferably 30% or more, more preferably 50% or more, and further preferably 70% or more. In this case, more excellent performance can be expected, in terms of heat resistance and the expression of low linear thermal expansion. The crystallinity can be obtained by measuring an X-ray diffraction profile and obtaining it according to a common method (Seagal et al., Textile Research Journal, Vol. 29, p. 786, 1959).

The ultrafine cellulose fibers preferably have phosphoric acid groups or substituents derived from the phosphoric acid group. The phosphoric acid group is a divalent functional group corresponding to a phosphoric acid from which a hydroxyl group is removed. Specifically, it is a group represented by —PO$_3$H$_2$. The substituents derived from the phosphoric acid group may include substituents, such as condensation-polymerized phosphoric acid groups, salts of phosphoric acid groups, and phosphoric acid ester groups, and they may be either ionic substituents or nonionic substituents.

In the present invention, the phosphoric acid group or the phosphoric acid group-derived substituent may be a substituent represented by the following formula (1):

[Formula 1]

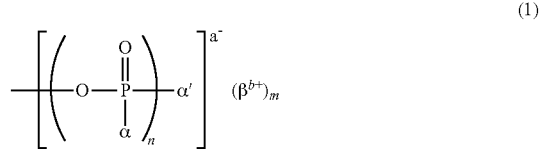

wherein a, b, m, and n each independently represent an integer (provided that a=b×m). In addition, α and α' each independently represent R or OR. R represents a hydrogen atom, a saturated straight chain hydrocarbon group, a saturated branched chain hydrocarbon group, a saturated cyclic hydrocarbon group, an unsaturated straight chain hydrocarbon group, an unsaturated branched chain hydrocarbon group, an aromatic group, or a derivative thereof. β represents a mono- or more-valent cation consisting of an organic or inorganic matter.

<Introduction of Phosphoric Acid Groups>

Introduction of phosphoric acid groups may be carried out by allowing at least one selected from a compound having phosphoric acid groups and salts thereof (hereinafter, referred to as a "phosphorylating reagent" or "Compound A") to react with the fiber raw material including cellulose. Such a phosphorylating reagent may be mixed into the fiber raw material in a dry or wet state, in the form of a powder or an aqueous solution. In another example, a powder or an aqueous solution of the phosphorylating reagent may be added into a slurry of the fiber raw material.

Introduction of phosphoric acid groups may be carried out by allowing at least one selected from a compound having phosphoric acid groups and salts thereof (a phosphorylating reagent or Compound A) to react with the fiber raw material including cellulose. It is to be noted that this reaction may be carried out in the presence of at least one selected from urea and derivatives thereof (hereinafter, referred to as "Compound B").

One example of the method of allowing Compound A to act on the fiber raw material in the presence of Compound B includes a method of mixing the fiber raw material in a dry or wet state with a powder or an aqueous solution of Compound A and Compound B. Another example thereof includes a method of adding a powder or an aqueous solution of Compound A and Compound B to a slurry of the fiber raw material. Among them, a method of adding an aqueous solution of Compound A and Compound B to the fiber raw material in a dry state, or a method of adding a powder or an aqueous solution of Compound A and Compound B to the fiber raw material in a wet state is preferable because of the high homogeneity of the reaction. Compound A and Compound B may be added at the same time or may be added separately. Alternatively, Compound A and Compound B to be subjected to the reaction may be first added as an aqueous solution, which may be then compressed to squeeze out redundant chemicals. The form of the fiber raw material is preferably a cotton-like or thin sheet form, but the form is not particularly limited thereto.

The Compound A used in the present embodiment is at least one selected from a compound having a phosphoric acid group or a salt thereof.

Examples of the compound having a phosphoric acid group include, but are not particularly limited to, phosphoric acid, lithium salts of phosphoric acid, sodium salts of phosphoric acid, potassium salts of phosphoric acid, and ammonium salts of phosphoric acid. Examples of the lithium salts of phosphoric acid include lithium dihydrogen phosphate, dilithium hydrogen phosphate, trilithium phosphate, lithium pyrophosphate, and lithium polyphosphate. Examples of the sodium salts of phosphoric acid include sodium dihydrogen phosphate, disodium hydrogen phosphate, trisodium phosphate, sodium pyrophosphate, and sodium polyphosphate. Examples of the potassium salts of phosphoric acid include potassium dihydrogen phosphate, dipotassium hydrogen phosphate, tripotassium phosphate, potassium pyrophosphate, and potassium polyphosphate. Examples of the ammonium salts of phosphoric acid include ammonium dihydrogen phosphate, diammonium hydrogen phosphate, triammonium phosphate, ammonium pyrophosphate, and ammonium polyphosphate.

Among them, from the viewpoints of high efficiency in introduction of the phosphoric acid group, an improving tendency of the defibration efficiency in a defibration step described below, low cost, and industrial applicability, phosphoric acid, sodium phosphate, potassium phosphate, and ammonium phosphate are preferable. Sodium dihydrogen phosphate, or disodium hydrogen phosphate is more preferable.

Further, since the uniformity of the reaction is improved and the efficiency in introduction of a phosphoric acid group is enhanced, the Compound A is preferably used as an aqueous solution. Although there is no particular restriction on the pH of an aqueous solution of the Compound A, the pH is preferably pH 7 or less because the efficiency in introduction of a phosphoric acid group is high, and more preferably pH 3 or more and pH 7 or less from the viewpoint of suppression of hydrolysis of a pulp fiber. The pH of an aqueous solution of the Compound A may be adjusted, for example, by using, among compounds having a phosphoric acid group, a combination of an acidic one and an alkaline one, and changing the amount ratio thereof. The pH of an aqueous solution of Compound A may also be adjusted by adding an inorganic alkali or an organic alkali to an acidic compound among compounds having a phosphoric acid group.

Although there is no particular restriction on the amount of the Compound A added to a fiber raw material, if the amount of the Compound A added is converted to a phosphorus atomic weight, the amount of phosphorus atoms added with respect to the fiber raw material (absolute dry mass) is preferably 0.5% by mass or more and 100% by mass or less, more preferably 1% by mass or more and 50% by mass or less, and most preferably 2% by mass or more and 30% by mass or less. When the amount of phosphorus atoms added to the fiber raw material is within the above-described range, the yield of ultrafine cellulose fibers can be further improved. On the other hand, by setting the amount of phosphorus atoms added to the fiber raw material at 100% by mass or less, the cost of the used Compound A can be suppressed, while enhancing phosphorylation efficiency.

Examples of the Compound B used in the present embodiment include urea, biuret, 1-phenyl urea, 1-benzyl urea, 1-methyl urea, and 1-ethyl urea.

The Compound B is preferably used as an aqueous solution, as with the Compound A. Further, an aqueous solution in which both the Compound A and Compound B are dissolved is preferably used, because the uniformity of a reaction may be enhanced. The amount of the Compound B added to a fiber raw material (absolute dry mass) is preferably 1% by mass or more and 500% by mass or less, more preferably 10% by mass or more and 400% by mass or less, further preferably 100% by mass or more and 350% by mass or less, and particularly preferably 150% by mass or more and 300% by mass or less.

The reaction system may comprise an amide or an amine, in addition to the Compound A and the Compound B. Examples of the amide include formamide, dimethylformamide, acetamide, and dimethylacetamide. Examples of the amine include methylamine, ethylamine, trimethylamine, triethylamine, monoethanolamine, diethanolamine, triethanolamine, pyridine, ethylenediamine, and hexamethylenediamine. Among them, particularly, triethylamine is known to work as a favorable reaction catalyst.

In the phosphoric acid group introduction step, it is preferable to perform a heat treatment. For the temperature of such a heat treatment, it is preferable to select a temperature that allows an efficient introduction of phosphoric acid groups, while suppressing the thermal decomposition or hydrolysis reaction of fibers. Specifically, the temperature is preferably 50° C. or higher and 300° C. or lower, more preferably 100° C. or higher and 250° C. or lower, and further preferably 130° C. or higher and 200° C. or lower. In addition, a vacuum dryer, an infrared heating device, or a microwave heating device may be used for heating.

Upon the heat treatment, if the time for leaving the fiber raw material to stand still gets longer while the fiber raw material slurry to which the Compound A is added contains water, as drying advances, water molecules and the Compound A dissolved therein move to the surface of the fiber raw material. As such, there is a possibility of the occurrence of unevenness in the concentration of the Compound A in the fiber raw material, and the introduction of phosphoric acid groups to the fiber surface may not progress uniformly. In order to suppress the occurrence of unevenness in the concentration of the Compound A in the fiber raw material due to drying, the fiber raw material in the shape of a very thin sheet may be used, or a method of heat-drying or vacuum-drying the fiber raw material, while kneading or stirring with the Compound A using a kneader or the like, may be employed.

As a heating device used for heat treatment, a device capable of always discharging moisture retained by slurry or moisture generated by an addition reaction of phosphoric acid groups with hydroxy groups of the fiber to the outside of the device system is preferable, and for example, forced convection ovens or the like are preferable. By always discharging moisture in the device system, in addition to being able to suppress a hydrolysis reaction of phosphoric acid ester bonds, which is a reverse reaction of the phosphoric acid esterification, acid hydrolysis of sugar chains in the fiber may be suppressed as well, and ultrafine fibers with a high axial ratio can be obtained.

The time for heat treatment is, although affected by the heating temperature, preferably 1 second or more and 300 minutes or less, more preferably 1 second or more and 1000 seconds or less, and further preferably 10 seconds or more and 800 seconds or less, after moisture is substantially removed from the fiber raw material slurry. In the present invention, by setting the heating temperature and heating time within an appropriate range, the amount of phosphoric acid groups introduced can be set within a preferred range.

The amount of phosphoric acid groups introduced is, per 1 g (mass) of the ultrafine cellulose fibers, preferably 5.20 mmol/g or less, more preferably 0.1 mmol/g or more and 3.65 mmol/g or less, even more preferably 0.14 mmol/g or more and 3.5 mmol/g or less, further preferably 0.2 mmol/g or more and 3.2 mmol/g or less, particularly preferably 0.4 mmol/g or more and 3.0 mmol/g or less, and most preferably 0.6 mmol/g or more and 2.5 mmol/g or less. By setting the amount of phosphoric acid groups introduced within the above-described range, it may become easy to perform fibrillation on the fiber raw material, and the stability of the ultrafine cellulose fibers can be enhanced. In addition, by setting the amount of phosphoric acid groups introduced within the above-described range, it becomes possible to keep the hydrogen bond between ultrafine cellulose fibers, while facilitating fibrillation, and thus, when a film is formed from the ultrafine cellulose fibers, the film is anticipated to have favorable strength.

The amount of phosphoric acid groups introduced into a fiber raw material may be measured by a conductometric titration method. Specifically, the amount introduced may be measured by performing fibrillation on ultrafine fibers in a defibration treatment step, treating the resulting slurry comprising ultrafine cellulose fibers with an ion exchange resin, and then examining a change in the electrical conductivity while adding an aqueous sodium hydroxide solution.

The conductometric titration confers a curve shown in FIG. 1 as an alkali is added. First, the electrical conductivity is rapidly reduced (hereinafter, this region is referred to as a "first region"). Then, the conductivity starts rising slightly (hereinafter, this region is referred to as a "second region"). Then, the increment of the conductivity is increased (hereinafter, this region is referred to as a "third region"). In short, three regions appear. The boundary point between the second region and the third region is defined as a point at which a change amount in the two differential values of conductivity, namely, an increase in the conductivity (inclination) becomes maximum. Among them, the amount of the alkali required for the first region among these regions is equal to the amount of a strongly acidic group in the slurry used in the titration, and the amount of the alkali required for the second region is equal to the amount of a weakly acidic group in the slurry used in the titration. When condensation of a phosphoric acid group occurs, the weakly acidic group is apparently lost, so that the amount of the alkali required for the second region is decreased as compared with the amount of the alkali required for the first region. On the other hand, the amount of the strongly acidic group agrees with the amount of the phosphorus atom regardless of the presence or absence of condensation. Therefore, the simple term "the amount of the phosphoric acid group introduced (or the amount of the phosphoric acid group)" or "the amount of the substituent introduced (or the amount of the substituent)" refers to the amount of the strongly acidic group. That is to say, the amount (mmol) of the alkali required for the first region in the curve shown in FIG. 1 is divided by the solid content (g) in the slurry as a titration target to obtain the amount (mmol/g) of the substituent introduced.

The phosphoric acid group introduction step may be performed at least once, but may be repeated multiple times as well. This case is preferable, since more phosphoric acid groups are introduced.

<Introduction of Carboxyl Groups>

In the present invention, when the ultrafine cellulose fibers have carboxyl groups, such carboxyl groups can be introduced into the ultrafine cellulose fibers, for example, by performing an oxidation treatment such as a TEMPO (2,2,6,6-tetramethylpiperidin-1-oxyl) oxidation treatment on the fiber raw material, or by treating the ultrafine cellulose fibers with a compound having groups derived from carboxylic acid, a derivative thereof, or an acid anhydride thereof or a derivative thereof.

Examples of the compound having a carboxyl group include, but are not particularly limited to, dicarboxylic acid compounds such as maleic acid, succinic acid, phthalic acid, fumaric acid, glutaric acid, adipic acid or itaconic acid, and tricarboxylic acid compounds such as citric acid or aconitic acid.

Examples of the acid anhydride of the compound having a carboxyl group include, but are not particularly limited to, acid anhydrides of dicarboxylic acid compounds, such as maleic anhydride, succinic anhydride, phthalic anhydride, glutaric anhydride, adipic anhydride, or itaconic anhydride.

Examples of the derivative of the compound having a carboxyl group include, but are not particularly limited to, an imidized product of the acid anhydride of the compound having a carboxyl group and a derivative of the acid anhydride of the compound having a carboxyl group. Examples of the imidized product of the acid anhydride of the compound having a carboxyl group include, but are not particularly limited to, imidized products of dicarboxylic acid compounds, such as maleimide, succinimide, or phthalimide.

The derivative of the acid anhydride of the compound having a carboxyl group is not particularly limited. Examples include acid anhydrides of the compounds having a carboxyl group, in which at least some hydrogen atoms are substituted with substituents (for example, an alkyl group, a phenyl group, etc.), such as dimethylmaleic anhydride, diethylmaleic anhydride, or diphenylmaleic anhydride.

The amount of carboxyl groups introduced is, per 1 g (mass) of the ultrafine cellulose fibers, preferably 0.1 mmol/g or more and 3.65 mmol/g or less, more preferably 0.14 mmol/g or more and 3.5 mmol/g or less, further preferably 0.2 mmol/g or more and 3.2 mmol/g or less, particularly preferably 0.4 mmol/g or more and 3.0 mmol/g or less, and most preferably 0.6 mmol/g or more and 2.5 mmol/g or less.

The amount of carboxyl groups introduced into a fiber raw material can be measured by a conductometric titration method. In conductometric titration, addition of alkali gives the curve shown in FIG. 2. The amount of the alkali (mmol) required for the first region in the curve shown in FIG. 2 is divided by the solid content (g) in the slurry to be titrated to determine the amount of the substituents introduced (mmol/g).

<Alkali Treatment>

When the ultrafine cellulose fibers are produced, an alkali treatment may be conducted between an ionic functional group introduction step and a defibration treatment step described below. The method of the alkali treatment is not particularly limited. For example, a method of immersing functional group-introduced fibers in an alkaline solution may be applied.

The alkali compound contained in the alkaline solution is not particularly limited, and it may be an inorganic alkaline compound or an organic alkali compound. The solvent of the alkaline solution may be either water or an organic solvent. The solvent is preferably a polar solvent (water, or a polar organic solvent such as alcohol), and more preferably an aqueous solvent containing, at least, water.

Among alkaline solutions, a sodium hydroxide aqueous solution, or a potassium hydroxide aqueous solution is particularly preferable, because of high versatility.

The temperature of the alkali solution in the alkali treatment step is not particularly limited, and it is preferably 5° C. or higher and 80° C. or lower, and more preferably 10° C. or higher and 60° C. or lower.

The immersion time in the alkali solution in the alkali treatment step is not particularly limited, and it is preferably 5 minutes or more and 30 minutes or less, and more preferably 10 minutes or more and 20 minutes or less.

The amount of the alkali solution used in the alkali treatment is not particularly limited, and it is preferably 100% by mass or more and 100000% by mass or less, and more preferably 1000% by mass and 10000% by mass or less, with respect to the absolute dry mass of the phosphoric acid group-introduced fibers.

In order to reduce the amount of an alkaline solution used in the alkali treatment step, functional group-introduced fibers may be washed with water or an organic solvent before the alkali treatment step. After the alkali treatment, the alkali-treated functional group-introduced fibers are preferably washed with water or an organic solvent before the defibration treatment step in order to improve the handling property.

<Defibration Treatment>

Cellulose fibers are subjected to a defibration treatment in a defibration treatment step. In the defibration treatment step, fibers are defibrated usually using a defibration treatment apparatus to yield a slurry containing ultrafine cellulose fibers, and there is no particular restriction on a treatment apparatus, or a treatment method.

A high-speed defibrator, a grinder (stone mill-type crusher), a high-pressure homogenizer, an ultrahigh-pressure homogenizer, a high-pressure collision-type crusher, a ball mill, a bead mill, or the like can be used as the defibration treatment apparatus. Alternatively, for example, a wet milling apparatus such as a disc-type refiner, a conical refiner, a twin-screw kneader, an oscillation mill, a homomixer under high-speed rotation, an ultrasonic disperser, or a beater may also be used as the defibration treatment apparatus. The defibration treatment apparatus is not limited to the above. Examples of a preferred defibration treatment method may include a high-speed defibrator, a high-pressure homogenizer, and an ultrahigh-pressure homogenizer, which are less affected by milling media, and are less likely to be contaminated.

Upon the defibration treatment, the fiber raw material is preferably diluted with water and an organic solvent each alone or in combination, to prepare a slurry, though the method is not particularly limited thereto. Water as well as a polar organic solvent can be used as a dispersion medium. Preferred examples of the polar organic solvent may include, but are not particularly limited to, alcohols, ketones, ethers, dimethyl sulfoxide (DMSO), dimethylfonmamide (DMF), and dimethylacetamide (DMAc). Examples of the alcohols may include methanol, ethanol, n-propanol, isopropanol, n-butanol, and t-butyl alcohol. Examples of the ketones may include acetone and methyl ethyl ketone (MEK). Examples of the ethers may include diethyl ether and tetrahydrofuran (THF). One of these dispersion media may be used, or two or more thereof may be used. The dispersion medium may also contain a solid content other than the fiber raw material, for example, hydrogen-binding urea.

With regard to the ultrafine cellulose fibers, the ultrafine cellulose fiber-containing slurry obtained by the defibration treatment may be once concentrated and/or dried, and then, may be subjected to a defibration treatment again. In this case, there is no particular restriction on the method of concentration and drying, but examples thereof may include a method in which a concentrating agent is added into a slurry comprising ultrafine cellulose fibers, and a method using a dehydrator, a press, a dryer, and the like used generally. Further, publicly known methods, for example as described in WO 2014/024876, WO 2012/107642, and WO 2013/121086, may be used. Also, the ultrafine cellulose fiber-containing slurry may be formed into a sheet, so that it is concentrated and dried. The formed sheet is subjected to a defibration treatment, so that an ultrafine cellulose fiber-containing slurry can be obtained again.

Examples of a device used for defibrating (pulverizing) the ultrafine cellulose fiber-containing slurry again, after the concentration and/or drying of the ultrafine cellulose fiber-containing slurry, may include, but are not particularly limited to, a high-speed defibrator, a grinder (stone mill-type grinder), a high-pressure homogenizer, an ultra-high pressure homogenizer, a high-pressure collision type crusher, a ball mill, a bead mill, a disk type refiner, a conical refiner, a twin screw kneader, a vibrating mill, and a device for wet milling, such as a high-speed rotating homomixer, an ultrasonic disperser, or a beater.

<Enzyme Treatment>

The cellulose-containing composition of the present invention comprises protein, and the protein includes an enzyme.

It is to be noted that the term "protein" used in the present embodiment means the added enzyme. Thus, in the present embodiment, the amount of protein is identical to the amount of an enzyme. In addition, in the present embodiment, when an enzyme is inactivated after completion of an enzyme treatment, the inactivated enzyme and a non-inactivated enzyme are collectively referred to as protein. The phrase "the cellulose-containing composition of the present invention comprises protein, and the protein includes an enzyme" means that the cellulose-containing composition comprises either one of or both of the inactivated enzyme and an enzyme that is not inactivated and has activity.

The enzyme used in the present invention is a cellulase enzyme, which is classified into a glycoside hydrolase family that is based on a higher-order structure of a catalytic domain having cellulose hydrolysis reaction function. The cellulase enzyme is classified into endo-glucanase and cellobiohydrolase, depending on cellulose-decomposing properties. Endo-glucanase has high hydrolyzability to amorphous portions of cellulose, soluble cellooligosaccharides, or cellulose derivatives such as carboxymethyl cellulose, and randomly cleaves their molecular chains from the inside, so as to reduce the polymerization degree. On the other hand, endo-glucanase has low hydrolytic reactivity to cellulose microfibrils having crystallinity. In contrast, cellobiohydrolase decomposes crystalline portions of cellulose and gives cellobiose. In addition, cellobiohydrolase hydrolyzes cellulose from the termini of cellulose molecules, and is also referred to as "exo-type enzyme" or "processive enzyme." In the present invention, endo-glucanase is preferably used.

The enzyme used in the present invention may also include hemicellulase enzymes, as well as endo-glucanase and cellobiohydrolase. Examples of such hemicellulase enzyme may include xylanase that is an enzyme decomposing xylan, mannase that is an enzyme decomposing mannan, and arabanase that is an enzyme decomposing araban. Moreover, pectinase that is an enzyme decomposing pectin can also be used as a hemicellulase enzyme. Microorganisms generating hemicellulase enzymes also generate cellulase enzymes in many cases.

Hemicelluloses are polysaccharides excluding pectins, which are present among cellulose microfibrils in plant cell walls. There are a wide variety of hemicelluloses, and they are different, even depending on the types of plants or among the wall layers of cell walls. Regarding woods, glucomannan is a main ingredient of the secondary wall of a needle leaf tree, whereas 4-O-methylglucuronoxylan is a main ingredient of the secondary wall of a broad leaf tree. Hence, in order to obtain ultrafine fibers from needle leaf trees, mannase is preferably used. In the case of broad leaf trees, xylanase is preferably used.

According to the present invention, provided is a method for producing a cellulose-containing composition, comprising a step of adding an enzyme in an amount of $1 \times 10^{-3}$ parts by mass or less with respect to 1 part by mass of cellulose fibers having a fiber width of 1000 nm or less. By adding an enzyme to ultrafine cellulose fibers, the ultrafine cellulose fibers can be reacted with the enzyme. In the present invention, an embodiment, in which a step of washing ultrafine cellulose fibers is not carried out after completion of the enzyme treatment, can be adopted.

In the present invention, the enzyme may be inactivated after completion of the enzyme treatment. Examples of the method of inactivating the enzyme may include, but are not limited to: a method comprising heating a mixture of ultrafine cellulose fibers and an enzyme to 100° C., and then, while keeping the temperature at 100° C., leaving the mixture at rest for 30 minutes to 1 hour, and a method comprising adding a strong base to a mixture of ultrafine cellulose fibers and an enzyme to adjust a pH value to pH 10 or more.

According to the above-described method for producing a cellulose-containing composition, the cellulose-containing composition of the present invention can be produced.

The amount of an enzyme added with respect to 1 part by mass of cellulose fibers having a fiber width of 1000 nm or less may be $1 \times 10^{-3}$ parts by mass or less. The amount of the enzyme added is preferably $1 \times 10^{-4}$ parts by mass or less, more preferably $1 \times 10^{-5}$ parts by mass or less, and particularly preferably $5.0 \times 10^{-6}$ parts by mass or less. On the other hand, the amount of an enzyme added is preferably $1 \times 10^{-7}$ parts by mass or more, more preferably $3 \times 10^{-7}$ parts by mass or more, and further preferably $1 \times 10^{-6}$ parts by mass or more, with respect to 1 part by mass of the cellulose fibers.

By setting the amount of the enzyme added within the above-described range, the produced cellulose-containing composition can achieve favorable coating suitability.

The reaction time for the reaction of the ultrafine cellulose fibers with the enzyme is not particularly limited. In general, the reaction time is preferably 1 minute to 24 hours, and more preferably 1 minute to 1 hour.

The reaction temperature and the reaction pH applied to the reaction of the ultrafine cellulose fibers with the enzyme are preferably kept to the temperature and pH optimal to the used enzyme. In general, the reaction temperature and the reaction pH are preferably kept at 20° C. to 80° C., and at pH 4.5 to 9.5.

By setting the reaction conditions within the above-described range, the produced cellulose-containing composition can achieve favorable coating suitability.

<Polymerization Degree>

The polymerization degree of cellulose fibers in the cellulose-containing composition of the present invention is not particularly limited, and it is preferably 200 or more and 450 or less, more preferably 250 or more and 400 or less, further preferably 250 or more and 350 or less, and particularly preferably 270 or more and 300 or less.

The polymerization degree of cellulose fibers is calculated with reference to the following study papers.

TAPPI International Standard; ISO/FDIS 5351, 2009.

Smith, D. K.; Bampton, R. F.; Alexander, W. J. Ind. Eng. Chem., Process Des. Dev. 1963, 2, 57-62.

Specifically, 30 g of a suspension prepared by diluting ultrafine cellulose fibers with ion exchange water to a content of 2±0.3% by mass is fractionated into a centrifuge tube, and is then left at rest in a freezer overnight, so that the suspension is frozen. Further, the suspension is dried in a freeze-dryer for 5 days or more, and is then heated in a constant-temperature dryer set at 105° C. for 3 hours or more and 4 hours or less, so as to obtain ultrafine cellulose fibers that are in an absolute dry state.

In order to measure the reference, 15 ml of pure water and 15 ml of 1 mol/L copper ethylenediamine are added to a 50 ml-volume empty screw tube to prepare a 0.5 mol/L copper ethylenediamine solution. Into a Cannon-Fenske viscometer, 10 ml of the aforementioned 0.5 mol/L copper ethylenediamine solution is placed, and it is then left for 5 minutes. Thereafter, the fall time at 25° C. is measured, and it is defined as a solvent fall time.

Subsequently, in order to measure the viscosity of the ultrafine cellulose fibers, 0.14 g or more and 0.16 g or less of the absolutely dried ultrafine cellulose fibers are weighed into a 50 ml-volume empty screw tube, and 15 ml of pure water is then added thereto. Further, 15 ml of 1 mol/L copper ethylenediamine is added thereto, and the obtained mixture is then stirred using a planetary centrifugal super-mixer at 1000 rpm for 10 minutes, so as to obtain a 0.5 mol/L copper ethylenediamine solution, in which the ultrafine cellulose fibers are dissolved. As in the case of the measurement of the reference, 10 ml of the prepared 0.5 mol/L copper ethylenediamine solution is placed in a Cannon-Fenske viscometer, and is then left for 5 minutes, and thereafter, the fall time at 25° C. is measured. The measurement of the fall time is carried out three times, and the mean value thereof is defined to be the fall time of an ultrafine cellulose fiber-containing solution.

Using the mass of the absolutely dried ultrafine cellulose fibers used in the measurement, the solvent fall time, and the fall time of the ultrafine cellulose fiber-containing solution, the polymerization degree is calculated according to the following equation. When the measurement is carried out two or more times, the following average polymerization degree is a mean value of individual measurements.

Mass of absolutely dried ultrafine cellulose fibers used in measurement: a (g) (wherein a is 0.14 or more and 0.16 or less)

Cellulose concentration in solution: $c = a/30$ (g/mL)

Solvent fall time: $t_0$ (sec)

Fall time of ultrafine cellulose fiber-containing solution: t (sec)

Relative viscosity of solution: $\eta_{rel} = t/t_0$

Specific viscosity of solution: $\eta_{sp}=\eta_{rel}-1$
Intrinsic viscosity: $[\eta]=\eta_{sp}/c(1+0.28\ \eta_{sp})$
Polymerization degree: $DP=[\eta]/0.57$ Besides, since the average polymerization degree of ultrafine cellulose fibers is calculated according to the above-described method, it is also referred to as a "viscosity average polymerization degree."

(Hydrophilic Polymer)

The cellulose fiber-containing composition of the present invention may further comprise a hydrophilic polymer. In particular, when the cellulose fiber-containing composition is a slurry for use in formation of a coating film, it preferably comprises such a hydrophilic polymer. By allowing the slurry for use in formation of a coating film to comprise a hydrophilic polymer, an ultrafine cellulose fiber-containing film having high transparency and high mechanical strength can be obtained.

Examples of the hydrophilic polymer may include polyethylene glycol, cellulose derivatives (hydroxyethyl cellulose, carboxyethyl cellulose, carboxymethyl cellulose, etc.), casein, dextrin, starch, modified starch, polyvinyl alcohol, modified polyvinyl alcohol (acetoacetylated polyvinyl alcohol, etc.), polyethylene oxide, polyvinylpyrrolidone, polyvinyl methyl ether, polyacrylates, polyacrylamide, acrylic acid alkyl ester copolymers, and urethane copolymers. Among others, the hydrophilic polymer is preferably at least one type selected from polyethylene glycol (PEG), polyvinyl alcohol (PVA), modified polyvinyl alcohol (modified PVA) and polyethylene oxide (PEO), and is more preferably polyethylene oxide (PEO).

The content of the hydrophilic polymer is preferably 0.5 parts by mass or more, more preferably 3 parts by mass or more, further preferably 5 parts by mass or more, and particularly preferably 10 parts by mass or more, with respect to 100 parts by mass of the cellulose fibers. On the other hand, the content of the hydrophilic polymer is preferably 5000 parts by mass or less, more preferably 1000 parts by mass or less, further preferably 500 parts by mass or less, and particularly preferably 100 parts by mass or less, with respect to 100 parts by mass of the cellulose fibers.

The viscosity average molecular weight of the hydrophilic polymer is not particularly limited, and it is preferably $1.0\times10^3$ or more and $1.0\times10^7$ or less, more preferably $2.0\times10^3$ or more and $1.0\times10^7$ or less, and further preferably $5.0\times10^3$ or more and $1.0\times10^7$ or less.

(Optional Component)

The cellulose fiber-containing composition of the present invention may comprise optional components other than the aforementioned components. Examples of such optional components may include antifoaming agents, lubricants, ultraviolet absorbing agents, dyes, pigments, stabilizers, surfactants, coupling agents, inorganic layered compounds, inorganic compounds, leveling agents, organic particles, antistatic agents, magnetic powders, orientation promoters, plasticizers, antiseptics, and crosslinkers. Moreover, as such optional components, organic ions may also be added to the cellulose fiber-containing composition.

As such optional components, a thermoplastic resin, a thermosetting resin, a photocurable resin and the like may also be added. These resins may be added in the form of an emulsion. Specific examples of such a thermosetting resin emulsion and a photocurable resin emulsion may include those described in JP-A-2009-299043.

(Cellulose-Containing Film)

The present invention also relates to a cellulose-containing film formed from the aforementioned cellulose-containing composition. The present invention relates to a cellulose-containing film comprising cellulose fibers having a fiber width of 1000 nm or less and protein, wherein the protein includes an enzyme, and the content of the protein is $1\times10^{-3}$ parts by mass or less with respect to 1 part by mass of the cellulose fibers. It is to be noted that, in the description of the present application, the film includes a film laminated on another base material and a sheet detached from a base material etc.

The content of the protein in the cellulose-containing film may be $1\times10^{-3}$ parts by mass or less with respect to 1 part by mass of the cellulose fibers, and it is preferably $1\times10^{-4}$ parts by mass or less, more preferably $1\times10^{-5}$ parts by mass or less, and particularly preferably $5.0\times10^{-6}$ parts by mass or less. On the other hand, the content of the protein in the cellulose-containing film is preferably $1\times10^{-7}$ parts by mass or more, more preferably $3\times10^{-7}$ parts by mass or more, and further preferably $1\times10^{-6}$ parts by mass or more, with respect to 1 part by mass of the cellulose fibers.

The content of the protein in the cellulose-containing film can be regulated, for example, by adjusting the amount of an enzyme added, or by adjusting a process of producing ultrafine cellulose fibers, including an enzyme treatment. In the present embodiment, the amount of the protein in the cellulose-containing film can be adjusted, for example, by utilizing the timing of performing an enzyme treatment, or by not performing a washing step after completion of the enzyme treatment and before a film formation step. By setting the content of the protein in the cellulose-containing film to be $1\times10^{-3}$ parts by mass or less with respect to 1 part by mass of the cellulose fibers, the optical properties of the cellulose-containing film can be improved.

The haze of the cellulose-containing film of the present invention is preferably less than 2.0%, more preferably less than 1.5%, and further preferably less than 1.0%. The haze of a cellulose-containing film is a value measured in accordance with JIS K 7136, using a hazemeter (manufactured by MURAKAMI COLOR RESEARCH LABORATORY Co., Ltd.; HM-150).

The tensile elastic modulus of the cellulose-containing film of the present invention is preferably 1 GPa or more, more preferably 2 GPa or more, and further preferably 4 GPa or more. The upper limit of the tensile elastic modulus of the cellulose-containing film is not particularly limited. For example, it can be set to be 50 GPa or less. The tensile elastic modulus of the cellulose-containing film is a value measured in accordance with JIS P 8113, using a tension testing machine "Tensilon" (manufactured by A & D Company, Limited). Upon the measurement of the tensile elastic modulus, a test piece to be measured is prepared by humidity conditioning for 24 hours at 23° C. and a relative humidity of 50%, and the measurement is then carried out under conditions of 23° C. and a relative humidity of 50%.

The thickness of the cellulose-containing film of the present invention is not particularly limited, and it is preferably 5 μm or more, more preferably 10 μm or more, and further preferably 20 m or more. The upper limit of the thickness of the cellulose-containing film is not particularly limited. For example, it can be set to be 1000 μm or less. Besides, the thickness of the cellulose-containing film can be measured using a stylus thickness gauge (manufactured by Mahr; Millitron 1202 D).

The basis weight of the cellulose-containing film of the present invention is preferably 10 g/m$^2$ or more, more preferably 20 g/m$^2$ or more, and further preferably 30 g/m$^2$ or more. On the other hand, the basis weight of the cellulose-containing film is preferably 100 g/m$^2$ or less, and more preferably 80 g/m² or less. Herein, the basis weight of the cellulose-containing film may be calculated in accordance with JIS P 8124.

(Method of Forming Film)

The step of forming a cellulose-containing film includes a step of obtaining a slurry comprising cellulose fibers having a fiber width of 1000 nm or less and protein, and a step of applying this slurry onto a base material or a step of papermaking from the slurry.

In the step of obtaining a slurry, an enzyme may be added in an amount of $1\times10^{-3}$ parts by mass or less with respect to 1 part by mass of ultrafine cellulose fibers contained in the slurry.

In the step of obtaining a slurry, a hydrophilic polymer may be further added. In addition, other than such a hydrophilic polymer, polyamine polyamide epihalohydrin or a thermoplastic resin such as a polyester resin, an acrylic resin or a urethane resin may also be added. Thus, by adding a hydrophilic polymer and the like to the slurry, a cellulose-containing film having excellent transparency and mechanical strength can be formed. Besides, when a hydrophilic polymer and the like are added, such a hydrophilic polymer and the like may be added before addition of an enzyme to ultrafine cellulose fibers.

<Coating Step>

The coating step is a step of applying the slurry obtained in the step of obtaining a slurry onto a base material, and then drying the slurry to form a film. The formed cellulose-containing film may be used without being detached from the base material, but it may also be used as a single sheet by being detached from the base material. Use of a coating apparatus and a long base material can continuously produce cellulose-containing films.

The material of the base material used in the coating step is not particularly limited. A base material having higher wettability to the composition (slurry) is preferable because the shrinkage of the cellulose-containing film or the like upon drying is suppressed. When the cellulose-containing film is used after it is detached from the base material, it is preferable to select one from which the cellulose-containing film formed after drying can be easily detached. Of these, a resin film or plate, or a metal film or plate is preferable, but is not particularly limited thereto. Examples of the base material that can be used herein may include: resin films or plates, such as those made of acryl, polyethylene terephthalate, vinyl chloride, polystyrene, or polyvinylidene chloride; metal films or plates, such as those made of aluminum, zinc, copper, or iron; these films or plates obtained by the oxidation treatment of surfaces thereof; and stainless films or plates and brass films or plates.

When the slurry has a low viscosity and spreads on the base material in the coating step, a damming frame may be fixed and used on the base material in order to obtain a cellulose-containing film having a predetermined thickness and basis weight. The quality of the damming frame is not particularly limited, and it is preferable to select ones from which the edges of the cellulose-containing film that adhere after drying can be easily detached. Of these, frames formed from resin plates or metal plates are preferable, without particular limitation. Example thereof that can be used herein may include frames formed from resin plates such as acrylic plates, polyethylene terephthalate plates, vinyl chloride plates, polystyrene plates, and polyvinylidene chloride plates; from metal plates such as aluminum plates, zinc plates, copper plates, and iron plates; from plates obtained by the oxidation treatment of surfaces thereof; and from stainless plates and brass plates.

Examples of a coater for applying the slurry that can be used herein may include roll coaters, gravure coaters, die coaters, curtain coaters, and air doctor coaters. Die coaters, curtain coaters, and spray coaters are preferable because more even thickness can be provided.

The coating temperature is not particularly limited, and it is preferably 20° C. or higher and 45° C. or lower, more preferably 25° C. or higher and 40° C. or lower, and further preferably 27° C. or higher and 35° C. or lower. When the coating temperature is equal to or higher than the above-described lower limit value, it is possible to easily apply the slurry. When the coating temperature is equal to or lower than the above-described upper limit value, it is possible to suppress volatilization of the dispersion medium upon coating.

In the coating step, it is preferable to apply the slurry so as to achieve a finished basis weight of the cellulose-containing film that is 10 g/m² or more and 100 g/m² or less, and preferably, 20 g/m² or more and 60 g/m² or less. By applying the slurry so as to achieve a basis weight that is within the above-described range, a cellulose-containing film having excellent strength can be obtained.

The coating step preferably includes a step of drying the slurry applied onto the base material. The drying method is not particularly limited, and either a contactless drying method or a method of drying the cellulose-containing film while locking the cellulose-containing film may be used, or these methods may also be used in combination.

The contactless drying method is not particularly limited, and a method for drying by heating with hot air, infrared radiation, far-infrared radiation, or near-infrared radiation (a drying method by heating) or a method for drying in vacuum (a vacuum drying method) can be utilized. Although the drying method by heating and the vacuum drying method may be combined, the drying method by heating is usually utilized. The drying with infrared radiation, far-infrared radiation, or near-infrared radiation can be performed using an infrared apparatus, a far-infrared apparatus, or a near-infrared apparatus without particular limitations. The heating temperature for the drying method by heating is not particularly limited, and it is preferably 20° C. or higher and 150° C. or lower, and more preferably 25° C. or higher and 105° C. or lower. At the heating temperature equal to or higher than the above-described lower limit value, the dispersion medium can be rapidly volatilized. At the heating temperature equal to or lower than the above-described upper limit value, cost required for the heating can be reduced, and the thermal discoloration of the ultrafine cellulose fibers can be suppressed.

<Papermaking Step>

The step of producing a cellulose-containing film may include a step of papermaking from a slurry. Examples of a paper machine used in the papermaking step may include continuous paper machines such as a Fourdrinier paper machine, a cylinder paper machine, and an inclined paper machine, and a multilayer combination paper machine, which is a combination thereof. Known papermaking such as papermaking by hand may be carried out in the papermaking step.

In the papermaking step, the slurry is wire-filtered and dehydrated to obtain a cellulose-containing film that is in a wet state. The cellulose-containing film is then pressed and dried to obtain a cellulose-containing film. Upon filtration and dehydration of the slurry, a filter fabric for filtration is not particularly limited. It is important that ultrafine cellulose fibers or antiseptics do not pass through the filter fabric and the filtration speed is not excessively slow. Such filter fabric is not particularly limited, and a cellulose-containing film consisting of an organic polymer, a woven fabric, or a porous membrane is preferable. Preferred examples of the organic polymer may include, but are not particularly limited to, non-cellulose organic polymers such as polyethylene terephthalate, polyethylene, polypropylene, and polytetrafluoroethylene (PTFE). Specific examples thereof may include, but are not particularly limited to, a polytetrafluoroethylene porous membrane having a pore size of 0.1 μm or more and 20 μm or less, for example, 1 μm, and woven fabric made of polyethylene terephthalate or polyethylene having a pore size of 0.1 μm or more and 20 μm or less, for example, 1 μm.

A method for producing a cellulose-containing film from a slurry is not particularly limited, and an example thereof is the method disclosed in WO 2011/013567 comprising using a production apparatus. This production apparatus comprises a dewatering section for ejecting an ultrafine cellulose fiber-containing slurry onto the upper surface of an endless belt and then dewatering a dispersion medium contained in the ejected slurry to form a web, and a drying section for drying the web to produce a fiber sheet. The endless belt is provided across from the dewatering section to the drying section, and the web formed in the dewatering section is transferred to the drying section while being placed on the endless belt.

The dehydration method that can be adopted in the present invention is not particularly limited. An example of the method is a dehydration method conventionally used for paper production. A preferred example is a method comprising performing dehydration using a Fourdrinier, cylinder, tilted wire, or the like and then performing dehydration using a roll press. In addition, a drying method is not particularly limited, and an example thereof is a method used for paper production and for example a method using a cylinder dryer, a yankee dryer, hot air drying, a near-infrared heater, or an infrared heater is preferable.

(Laminate)

A laminate may be formed by further laminating an additional layer on the cellulose-containing film obtained in the aforementioned step. Such an additional layer may be provided on both surfaces of the cellulose-containing film, or may also be provided on one surface of the cellulose-containing film. Examples of the additional layer that is laminated on at least one surface of the cellulose-containing film may include a resin layer and an inorganic layer.

Specific examples of the laminate may include:
a laminate in which a resin layer is directly laminated on at least one surface of a cellulose-containing film;
a laminate in which an inorganic layer is directly laminated on at least one surface of a cellulose-containing film;
a laminate in which a resin layer, a cellulose-containing film and an inorganic layer are laminated in this order,
a laminate in which a cellulose-containing film, a resin layer and an inorganic layer are laminated in this order, and
a laminate in which a cellulose-containing film, an inorganic layer and a resin layer are laminated in this order.

The layer configuration of the laminate is not limited to the above-described examples, and the laminate can have various aspects depending on intended use.

<Resin Layer>

The resin layer is a layer that has a natural resin or a synthetic resin as a main component. In this context, the main component refers to a component comprised in 50% by mass or more, based on the total mass of the resin layer. The content of the resin is preferably 60% by mass or more, more preferably 70% by mass or more, further preferably 80% by mass or more, and particularly preferably 90% by mass or more, based on the total mass of the resin layer. It is to be noted that the content of the resin may be set at 100% by mass, or may also be set at 95% by mass or less.

Examples of natural resins may include rosin-based resins, such as rosin, rosin ester and hydrated rosin ester.

The synthetic resin is preferably at least one selected from, for example, polycarbonate resins, polyethylene terephthalate resins, polyethylene naphthalate resins, polyethylene resins, polypropylene resins, polyimide resins, polystyrene resins, polyurethane resins and acrylic resins. Among them, the synthetic resin is preferably at least one selected from polycarbonate resins and acrylic resins, and more preferably a polycarbonate resin. It is to be noted that the acrylic resin is preferably at least any one selected from polyacrylonitrile and poly(meth)acrylate.

Examples of the polycarbonate resin, which constitutes the resin layer, may include aromatic polycarbonate-based resins and aliphatic polycarbonate-based resins. These specific polycarbonate-based resins are known, and a polycarbonate-based resin described in JP-A-2010-023275 is included, for example.

One resin that constitutes the resin layer may be used alone, or a copolymer obtained by copolymerization or graft polymerization of a plurality of resin components may be used. Alternatively, a plurality of resin components may be mixed by a physical process and used as a blend material.

An adhesive layer may be provided between the cellulose-containing film and the resin layer, or the cellulose-containing film and the resin layer may directly adhere to each other without providing an adhesive layer. When an adhesive layer is provided between the cellulose-containing film and the resin layer, examples of adhesives, which constitute the adhesive layer, may include acrylic resins. Examples of adhesives other than acrylic resins may include vinyl chloride resins, (meth)acrylic acid ester resins, styrene/acrylic acid ester copolymer resins, vinyl acetate resins, vinyl acetate/(meth)acrylic acid ester copolymer resins, urethane resins, silicone resins, epoxy resins, ethylene/vinyl acetate copolymer resins, polyester-based resins, polyvinyl alcohol resins, ethylene vinyl alcohol copolymer resins, and rubber-based emulsions such as SBR and NBR.

When no adhesive layer is provided between the cellulose-containing film and the resin layer, the resin layer may have an adhesion aid, or the surface of the resin layer may be surface-treated by a hydrophilization treatment or the like.

Examples of the adhesion aid may include compounds containing at least one selected from an isocyanate group, a carbodiimide group, an epoxy group, an oxazoline group, an amino group and a silanol group, and organic silicon compounds. Among them, the adhesion aid is preferably at least one selected from a compound containing an isocyanate group (isocyanate compound) and an organic silicon compound. Examples of the organic silicon compound may include silane coupling agent condensates and silane coupling agents.

Examples of the surface treatment method other than the hydrophilic treatment may include a corona treatment, a plasma discharge treatment, a UV irradiation treatment, an electron beam irradiation treatment, and a flame treatment.

<Inorganic Layer>

Substances constituting the inorganic layer are not particularly limited, and examples thereof may include aluminum, silicon, magnesium, zinc, tin, nickel, and titanium; oxides, carbides, nitrides, oxycarbides, oxynitrides, and oxycarbonitrides thereof; and mixtures thereof. From the viewpoint that high moisture resistance can be stably maintained, silicon oxide, silicon nitride, silicon oxycarbide, silicon oxynitride, silicon oxycarbonitride, aluminum oxide, aluminum nitride, aluminum oxycarbide, aluminum oxynitride, or mixtures thereof are preferable.

A method of forming an inorganic layer is not particularly limited. In general, methods of forming a thin film are roughly classified into Chemical Vapor Deposition (CVD) and Physical Vapor Deposition (PVD), either of which may be employed. Specific examples of CVD methods may include plasma CVD, which utilizes plasma, and Catalyst Chemical Vapor Deposition (Cat-CVD) including catalytically cracking material gas using a heated catalyzer. Specific examples of PVD methods may include vacuum deposition, ion plating, and sputtering.

As a method of forming an inorganic layer, Atomic Layer Deposition (ALD) can also be employed. The ALD method is a method of forming a thin film in an atomic layer unit by alternately supplying each of source gases of elements constituting the film to be formed to the surface on which a layer is to be formed. This method, albeit disadvantageous in a slow deposition rate, can more smoothly cover even a surface having a complicated shape than the plasma CVD method and has the advantage that a thin film having fewer defects can be formed. The ALD method also has the advantage that this method can control a film thickness at a nano order and can relatively easily cover a wide surface, for example. The ALD method can be further expected to improve a reaction rate, to achieve a low-temperature process, and to decrease unreacted gas, by using plasma.

(Intended Use)

The cellulose fiber-containing composition of the present invention can be used as a reinforcing material, by being mixed with, for example, a paint, a resin, an emulsion, a hydraulic material (cement), or a rubber. A film is formed using a slurry of the cellulose-containing composition of the present invention, so that a cellulose-containing film may be produced. The cellulose-containing composition of the present invention can also be used as a thickener for various types of intended uses.

The cellulose-containing film is suitable for intended uses such as light transmissive substrates for various display devices, various solar cells, and the like. In addition, the cellulose-containing film of the present invention is also suitable for intended uses, such as substrates of electronic devices, components of consumer electronics, window materials of various types of vehicles or buildings, interior materials, exterior materials, and wrapping materials. Moreover, the cellulose-containing film of the present invention is also suitable for intended uses, such as threads, filters, woven fabrics, buffering materials, sponges, and polishing materials, and also, other intended uses, in which the cellulose-containing film itself is used as a reinforcing material.

EXAMPLES

The characteristics of the present invention will be more specifically described in the following examples and comparative examples. The materials, used amounts, ratios, treatment contents, treatment procedures, etc. can be appropriately modified, unless they are deviated from the gist of the present invention. Accordingly, the scope of the present invention should not be restrictively interpreted by the following specific examples.

Example 1

<Production of Phosphoric Acid Group-Introduced Cellulose Fibers>

The needle bleached kraft pulp manufactured by Oji Paper Co., Ltd. (solid content: 93% by mass; basis weight: 208 g/m$^2$, sheet-shaped; and Canadian Standard Freeness (CSF) measured according to JIS P 8121 after defibration is 700 ml) was used as a raw material pulp.

A phosphorylation treatment was performed on this raw material pulp as follows.

First, a mixed aqueous solution of ammonium dihydrogen phosphate and urea was added to 100 parts by mass (absolute dry mass) of the above raw material pulp, and the obtained mixture was adjusted to result in 45 parts by mass of the ammonium dihydrogen phosphate, 120 parts by mass of the urea and 150 parts by mass of water, so as to obtain a chemical-impregnated pulp. Subsequently, the obtained chemical-impregnated pulp was heated in a hot-air dryer of 165° C. for 200 seconds, so that phosphoric acid groups were introduced into cellulose in the pulp, thereby obtaining a phosphorylated pulp.

Subsequently, a washing treatment was performed on the obtained phosphorylated pulp.

The washing treatment was carried out by repeating the operation to pour 10 L of ion exchange water onto 100 g (absolute dry mass) of the phosphorylated pulp to obtain a pulp dispersed solution, which was then uniformly dispersed by stirring, followed by filtration and dehydration. The washing was terminated at a time point at which the electric conductivity of the filtrate became 100 μS/cm or less.

Subsequently, an alkali treatment was performed on the phosphorylated pulp after the washing as follows.

First, the phosphorylated pulp after the washing was diluted with 10 L of ion exchange water, and then, while stirring, a 1 N sodium hydroxide aqueous solution was slowly added to the diluted solution to obtain a phosphorylated pulp slurry having a pH value of 12 or more and 13 or less. Thereafter, the phosphorylated pulp slurry was dehydrated, so as to obtain an alkali-treated phosphorylated pulp.

Subsequently, the above-described washing treatment was performed on the phosphorylated pulp after the alkali treatment.

The infrared absorption spectrum of the thus obtained phosphorylated pulp was measured by FT-IR. As a result, absorption based on the phosphoric acid groups was observed around 1230 cm$^{-1}$, and thus, addition of the phosphoric acid groups to the pulp was confirmed. In addition, the amount of phosphoric acid groups (the amount of strong acid groups) measured by the after-mentioned measurement method was 1.45 mmol/g.

Moreover, the obtained phosphorylated pulp was analyzed using an X-ray diffractometer. As a result, it was confirmed that there were typical peaks at two positions near $2\theta=14°$ or more and 17° or less, and near $2\theta=22°$ or more and 23° or less. Thus, the phosphorylated pulp was confirmed to have cellulose type I crystals.

<Defibration Treatment>

Ion exchange water was added to the obtained phosphorylated pulp, so as to prepare a slurry having a solid concentration of 2% by mass.

This slurry was treated using a wet atomization apparatus (manufactured by Sugino Machine Limited, Star Burst) at a pressure of 200 MPa four times to obtain an ultrafine cellulose fiber-dispersed solution A comprising ultrafine cellulose fibers.

It was confirmed according to X-ray diffraction that these ultrafine cellulose fibers maintained cellulose type I crystals.

Moreover, the fiber width of the ultrafine cellulose fibers was measured under a transmission electron microscope. As a result, the fiber width was 3 to 5 nm.

<Measurement of Amount of Phosphoric Acid Groups>

The amount of phosphoric acid groups in the ultrafine cellulose fibers was measured by treating with an ion exchange resin, a cellulose fiber-containing slurry prepared by diluting the ultrafine cellulose fiber-dispersed solution comprising ultrafine cellulose fibers as targets with ion exchange water to result in a content of 0.2% by mass, and then performing titration using alkali.

In the treatment with the ion exchange resin, 1/10 by volume of a strongly acidic ion exchange resin (Amberjet 1024; manufactured by Organo Corporation; conditioned) was added to the aforementioned cellulose fiber-containing slurry, and the resultant mixture was shaken for 1 hour. Then, the mixture was poured onto a mesh having 90-µm apertures to separate the resin from the slurry.

In the titration using alkali, a change in the electric conductivity value indicated by the slurry was measured while adding an aqueous solution of 0.1 N sodium hydroxide, once 30 seconds, in each amount of 50 µL, to the cellulose fiber-containing slurry after completion of the treatment with the ion exchange resin. Specifically, among the calculation results, the alkali amount (mmol) required in a region corresponding to the first region shown in FIG. 1 was divided by the solid content (g) in the slurry to be titrated, so as to obtain the amount of phosphoric acid groups (mmol/g).

<Measurement of Fiber Width>

The fiber width of ultrafine cellulose fibers was measured by the following method.

A supernatant of the ultrafine cellulose fiber-dispersed solution as obtained above by the treatment using a wet atomization apparatus was diluted with water, so that the concentration of the ultrafine cellulose fibers became 0.01% by mass or more and 0.1% by mass or less. The obtained solution was then added dropwise onto a hydrophilized carbon grid film. After drying, it was stained with uranyl acetate, and was then observed under a transmission electron microscope (manufactured by JEOL; JEOL-2000EX).

<Enzyme Treatment>

An enzyme-containing solution (manufactured by AB Enzymes, ECOPULP R, enzyme content: approximately 5% by mass) was added to the ultrafine cellulose fiber-dispersed solution A in an amount of $3.0 \times 10^{-6}$ pars by mass with respect to 1 part by mass of the ultrafine cellulose fibers, and the obtained mixture was then stirred at a rotation of 18,500 rpm for 2 minutes. The reaction mixture was recovered as a slurry to be evaluated.

Example 2

In <Enzyme treatment> of Example 1, the enzyme solution was added in an amount of $1.0 \times 10^{-2}$ parts by mass with respect to 1 part by mass of the ultrafine cellulose fibers. Other procedures were performed in the same manner as that of Example 1 to obtain a slurry to be evaluated.

Example 3

In <Enzyme treatment> of Example 1, the enzyme solution was added in an amount of $1.0 \times 10^{-5}$ parts by mass with respect to 1 part by mass of the ultrafine cellulose fibers. Other procedures were performed in the same manner as that of Example 1 to obtain a slurry to be evaluated.

Example 4

In <Enzyme treatment> of Example 1, the enzyme solution was added in an amount of $4.76 \times 10^{-5}$ parts by mass with respect to 1 part by mass of the ultrafine cellulose fibers. Other procedures were performed in the same manner as that of Example 1 to obtain a slurry to be evaluated.

Example 5

In Example 4, the after-mentioned ultrafine cellulose fiber-dispersed solution B was used instead of the ultrafine cellulose fiber-dispersed solution A. Other procedures were performed in the same manner as that of Example 4 to obtain a slurry to be evaluated. It is to be noted that the ultrafine cellulose fiber-dispersed solution B was produced by the following method.

<TEMPO Oxidation>

As a raw material pulp, the needle bleached kraft pulp (undried) manufactured by Oji Paper Co., Ltd. was used.

An alkali TEMPO oxidation treatment was performed on this raw material pulp as follows.

First, the above-described raw material pulp corresponding to 100 parts by mass (dry mass), 1.6 parts by mass of TEMPO (2,2,6,6-tetramethylpiperidin-1-oxyl), and 10 parts by mass of sodium bromide were dispersed in 10000 parts by mass of water. Subsequently, an aqueous solution containing 13% by mass of sodium hypochlorite was added to the obtained solution, such that the amount of sodium hypochlorite became 3.8 mmol with respect to 1.0 g of the pulp, so as to start the reaction. During the reaction, the pH was kept at pH 10 or more and pH 10.5 or less by the dropwise addition of a 0.5 M sodium hydroxide aqueous solution. The time point at which change in the pH was no longer seen was considered to be termination of the reaction.

<Washing of TEMPO-Oxidized Pulp>

Subsequently, a washing treatment was performed on the obtained TEMPO-oxidized pulp.

The washing treatment was carried out by repeating the operation of dehydrating the pulp slurry after the TEMPO oxidation to obtain a dehydrated sheet, then pouring 5000 parts by mass of ion exchange water onto the dehydrated sheet, which was then uniformly dispersed by stirring, and was then subjected to filtration and dehydration. The washing was terminated at a time point at which the electric conductivity of the filtrate became 100 µS/cm or less.

With respect to this dehydrated sheet, an additional oxidation treatment was performed on the remaining aldehyde groups as follows.

The above-described dehydrated sheet corresponding to 100 parts by mass (dry mass) was dispersed in 10000 parts by mass of a 0.1 mol/L acetate buffer (pH 4.8). Thereafter, 113 parts by mass of 80% sodium chlorite was added thereto, and the reaction system was immediately hermetically sealed. While the reaction mixture was stirred at 500 rpm using a magnetic stirrer, it was reacted at room temperature for 48 hours to obtain a pulp slurry.

Subsequently, a washing treatment was performed on the TEMPO-oxidized pulp obtained after the additional oxidation.

The washing treatment was carried out by repeating the operation of dehydrating the pulp slurry after the additional oxidation to obtain a dehydrated sheet, then pouring 5000 parts by mass of ion exchange water onto the dehydrated sheet, which was then uniformly dispersed by stirring, and was then subjected to filtration and dehydration. The washing was terminated at a time point at which the electric conductivity of the filtrate became 100 μS/cm or less. The amount of carboxyl groups in the thus obtained TEMPO-oxidized pulp, which was measured by the after-mentioned method, was 1.30 mmol/g.

The obtained TEMPO-oxidized pulp was analyzed using an X-ray diffractometer. As a result, it was confirmed that there were typical peaks at two positions near $2\theta=14°$ or more and 17° or less, and near $2\theta=22°$ or more and 23° or less. Thus, the TEMPO-oxidized pulp was confirmed to have cellulose type I crystals.

<Defibration Treatment>

Ion exchange water was added to the obtained dehydrated sheet, so as to prepare a slurry having a solid concentration of 2% by mass. This slurry was treated using a wet atomization apparatus (manufactured by Sugino Machine Limited, Star Burst) at a pressure of 200 MPa four times to obtain an ultrafine cellulose fiber-dispersed solution B.

<Measurement of Amount of Carboxyl Groups>

The amount of carboxyl groups in the ultrafine cellulose fibers was measured by adding ion exchange water to an ultrafine cellulose fiber-containing slurry comprising ultrafine cellulose fibers as targets to result in a content of 0.2% by mass, then treating the resulting slurry with ion exchange water, and then performing titration using alkali.

In the treatment with the ion exchange resin, 1/10 by volume of a strongly acidic ion exchange resin (Amberjet 1024; manufactured by Organo Corporation; conditioned) was added to 0.2% by mass of the ultrafine cellulose fiber-containing slurry, and the resultant mixture was shaken for 1 hour. Then, the mixture was poured onto a mesh having 90-μm apertures to separate the resin from the slurry.

In the titration using alkali, a change in the electric conductivity value indicated by the slurry was measured while adding a 0.1 N sodium hydroxide aqueous solution to the ultrafine cellulose fiber-containing slurry after completion of the treatment with the ion exchange resin. Specifically, among the calculation results, the alkali amount (mmol) required in a region corresponding to the first region shown in FIG. 2 was divided by the solid content (g) in the slurry to be titrated, so as to obtain the amount of carboxyl groups (mmol/g).

Comparative Example 1

<Enzyme treatment> was not performed in Example 1. Other than this, the procedures were carried out in the same manner as that of Example 1 to obtain a slurry to be evaluated.

Comparative Example 2

<Enzyme treatment>

The phosphorylated pulp after completion of the alkali treatment and the washing treatment, which had been obtained in <Production of phosphoric acid group-introduced cellulose fibers> of Example 1, was diluted with ion exchange water to a concentration of 2%, and an enzyme-containing solution was then added thereto. With regard to the amount of the enzyme-containing solution added, the enzyme-containing solution was added in an amount of $4.76\times10^{-5}$ parts by mass with respect to 1 part by mass of the solid content. Subsequently, this phosphorylated pulp was left at rest under the environment of 25° C. for 24 hours, and was then dehydrated to obtain a dehydration sheet. Then, 5000 parts by mass of ion exchange water was poured onto the dehydrated sheet, which was then uniformly dispersed by stirring, and was then subjected to filtration and dehydration. Thereafter, 5000 parts by mass of ion exchange water was poured onto the resultant again, which was then uniformly dispersed by stirring, and was then subjected to filtration and dehydration.

The amount of phosphoric acid groups (the amount of strong acid groups) in the above-described phosphorylated pulp after the filtration and dehydration, which was measured by the aforementioned method, was 1.45 mmol/g. In addition, the phosphorylated pulp was analyzed using an X-ray diffractometer. As a result, it was confirmed that there were typical peaks at two positions near $2\theta=14°$ or more and 17° or less, and near $2\theta=22°$ or more and 23° or less. Thus, the phosphorylated pulp was confirmed to have cellulose type I crystals.

<Defibration Treatment>

Ion exchange water was added to the obtained phosphorylated pulp, so as to prepare a slurry having a solid concentration of 2% by mass.

This slurry was treated using a wet atomization apparatus (manufactured by Sugino Machine Limited, Star Burst) at a pressure of 200 MPa four times to obtain a slurry to be evaluated, comprising ultrafine cellulose fibers.

It was confirmed according to X-ray diffraction that these ultrafine cellulose fibers maintained cellulose type I crystals.

Moreover, the fiber width of the ultrafine cellulose fibers was measured by the aforementioned method using a transmission electron microscope. As a result, the fiber width was 3 to 5 nm.

Comparative Example 3

The TEMPO-oxidized pulp after completion of the alkali treatment and the washing treatment, which had been obtained through <TEMPO oxidation> of Example 5, was diluted with ion exchange water to a concentration of 2%, and an enzyme-containing solution was then added thereto. With regard to the amount of the enzyme-containing solution added, the enzyme-containing solution was added in an amount of $4.76\times10^{-5}$ parts by mass with respect to 1 part by mass of the solid content. Subsequently, this TEMPO-oxidized pulp was left at rest under the environment of 25° C. for 24 hours, and was then dehydrated to obtain a dehydration sheet. Then, 5000 parts by mass of ion exchange water was poured onto the dehydrated sheet, which was then uniformly dispersed by stirring, and was then subjected to filtration and dehydration. Thereafter, 5000 parts by mass of ion exchange water was poured onto the resultant again, which was then uniformly dispersed by stirring, and was then subjected to filtration and dehydration.

The amount of carboxyl groups (the amount of strong acid groups) in the above-described TEMPO-oxidized pulp after the filtration and dehydration, which was measured by the aforementioned method, was 1.30 mmol/g. In addition, the TEMPO-oxidized pulp was analyzed using an X-ray diffractometer. As a result, it was confirmed that there were typical peaks at two positions near $2\theta=14°$ or more and 17° or less, and near $2\theta=22°$ or more and 23° or less. Thus, the TEMPO-oxidized pulp was confirmed to have cellulose type I crystals.

<Defibration Treatment>

Ion exchange water was added to the obtained dehydrated sheet, so as to prepare a slurry having a solid concentration of 2% by mass. This slurry was treated using a wet atomization apparatus (manufactured by Sugino Machine Limited, Star Burst) at a pressure of 200 MPa four times to obtain a slurry to be evaluated, comprising ultrafine cellulose fibers. It was confirmed according to X-ray diffraction that these ultrafine cellulose fibers maintained cellulose type 1 crystals. Moreover, the fiber width of the ultrafine cellulose fibers was measured by the aforementioned method using a transmission electron microscope. As a result, the fiber width was 3 to 5 nm.

Comparative Example 4

In Comparative Example 3, the amount of the enzyme-containing solution added was set to be $1.0 \times 10^{-1}$ parts by mass with respect to 1 part by mass of the solid content. Other than this, the procedures were carried out in the same manner as that of Comparative Example 3 to obtain a slurry to be evaluated.

Comparative Example 5

In Example 1, 1 part by mass of the enzyme-containing solution was added with respect to 1 part by mass of the ultrafine cellulose fibers. Other than this, the procedures were carried out in the same manner as that of Example 1 to obtain a slurry to be evaluated.

<Measurements>

The slurries to be evaluated, which were obtained in Example 1 to 5 and Comparative Examples 1 to 5, were measured according to the following methods.

[Viscosity]

Twenty-four hours after production of a slurry to be evaluated, ion exchange water was poured onto the slurry, so as to prepare a slurry having a solid concentration of 0.4% by mass. Thereafter, the resulting slurry was left at rest under the environment of 25° C. for 24 hours, and then, the viscosity of the slurry was measured using a Type B Viscometer (No. 3 Rotor) (manufactured by BROOKFIELD, analog viscometer T-LVT) at 25° C. at a rotation number of 3 rpm for 3 minutes.

[Polymerization Degree]

The average polymerization degree of cellulose molecules constituting ultrafine cellulose fibers was evaluated with reference to the following study papers.

TAPPI International Standard; ISO/FDIS 5351, 2009.

Smith, D. K.; Bampton, R. F.; Alexander, W. J. Ind. Eng. Chem., Process Des. Dev. 1963, 2, 57-62.

A suspension (30 g) prepared by diluting the ultrafine cellulose fibers as targets with ion exchange water to a content of 2±0.3% by mass was fractionated into a centrifuge tube, and was then left at rest in a freezer overnight, so that the suspension was frozen. Further, the suspension was dried in a freeze-dryer for 5 days or more, and was then heated in a constant-temperature dryer set at 105° C. for 3 hours or more and 4 hours or less, so as to obtain ultrafine cellulose fibers that are in an absolute dry state.

In order to measure the reference, 15 ml of pure water and 15 ml of 1 mol/L copper ethylenediamine were added to a 50 ml-volume empty screw tube to prepare a 0.5 mol/L copper ethylenediamine solution. Into a Cannon-Fenske viscometer, 10 ml of the aforementioned 0.5 mol/L copper ethylenediamine solution was placed, and it was then left for 5 minutes. Thereafter, the fall time at 25° C. was measured, and it was defined as a solvent fall time.

Subsequently, in order to measure the viscosity of the ultrafine cellulose fibers, 0.14 g or more and 0.16 g or less of the absolutely dried ultrafine cellulose fibers were weighed into a 50 ml-volume empty screw tube, and 15 ml of pure water was then added thereto. Further, 15 ml of 1 mol/L copper ethylenediamine was added thereto, and the obtained mixture was then stirred using a planetary centrifugal super-mixer at 1000 rpm for 10 minutes, so as to obtain a 0.5 mol/L copper ethylenediamine solution, in which the ultrafine cellulose fibers were dissolved. As in the case of the measurement of the reference, 10 ml of the prepared 0.5 mol/L copper ethylenediamine solution was placed in a Cannon-Fenske viscometer, and was then left for 5 minutes, and thereafter, the fall time at 25° C. was measured. The measurement of the fall time was carried out three times, and the mean value thereof was defined to be the fall time of an ultrafine cellulose fiber-containing solution.

Using the mass of the absolutely dried ultrafine cellulose fibers used in the measurement, the solvent fall time, and the fall time of the ultrafine cellulose fiber-containing solution, the polymerization degree was calculated according to the following equation. It is to be noted that the following average polymerization degree is a mean value of the values measured three times.

Mass of absolutely dried ultrafine cellulose fibers used in measurement: a (g) (wherein a is 0.14 or more and 0.16 or less)

Cellulose concentration in solution: $c=a/30$ (g/mL)

Solvent fall time: $t_0$ (sec)

Fall time of ultrafine cellulose fiber-containing solution: t (sec)

Relative viscosity of solution: $\eta_{rel}=t/t_0$

Specific viscosity of solution: $\eta_{sp}=\eta\eta_{rel}-1$

Intrinsic viscosity: $[\eta]=\eta_{sp}/c(1+0.28\,\eta_{sp})$

Polymerization degree: $DP=[\eta]/0.57$

[Endoglucanase (EG) Activity]

The EG activity of a slurry to be evaluated was measured and defined as follows.

A substrate solution (concentration: 100 mM; containing an acetate-sodium acetate buffer with pH 5.0) of 1% (W/V) carboxymethyl cellulose (CMCNa High viscosity: Cat No. 150561, MP Biomedicals, Inc.) was prepared. A slurry to be evaluated, immediately after the production thereof, had previously been diluted with a buffer (the same as described above) (wherein the dilution rate was determined, such that the absorbance of the following enzyme solution could be in the calibration curve obtained from the following glucose standard solution). To 90 μl of the above-described substrate solution, 10 μl of the above-diluted slurry solution to be evaluated was added, and the mixed solution was then reacted at 37° C. for 30 minutes.

In order to prepare a calibration curve, ion exchange water (blank) and glucose standard solutions (at least, 4 standard solutions each having a different concentration selected from a concentration of 0.5 to 5.6 mM) were selected, and these solutions were prepared in an amount of 100 μl each. The thus prepared solutions were incubated at 37° C. for 30 minutes.

After completion of the reaction, to each of the enzyme-containing slurry solution to be evaluated, the blank for the calibration curve, and the glucose standard solutions, 300 μl of DNS coloring solution (1.6% by mass of NaOH, 1% by mass of 3,5-dinitrosalicylic acid, and 30% by mass of potassium sodium tartrate) was added, and each mixed solution was boiled for 5 minutes for color development. Immediately after the color development, the reaction mixture was cooled on ice, and 2 ml of ion exchange water was then added thereto, followed by fully blending. The reaction mixture was left at rest for 30 minutes, and then, absorbance was measured within 1 hour.

Regarding the measurement of the absorbance, 200 μl of the reaction mixture was dispensed in a 96-well microwell plate (269620, manufactured by NUNC), and the absorbance at 540 nm was then measured using a microplate reader (infiniteM200, manufactured by TECAN).

Using the absorbance of each glucose standard solution, from which the absorbance of the blank was subtracted, and the glucose concentration, a calibration curve was produced. The amount of corresponding glucose generated in the slurry solution to be evaluated was calculated using the calibration curve, after subtracting the absorbance of the blank from the absorbance of the slurry solution to be evaluated (wherein when the absorbance of the slurry solution to be evaluated cannot in the calibration curve, the measurement was carried out again, while changing the dilution rate applied upon dilution of the slurry to be evaluated with the above-described buffer). The amount of an enzyme that generates reducing sugar equivalent to 1 μmol of glucose for 1 minute was defined as 1 unit, and EG activity is obtained according to the following equation:

EG activity=Amount (μmol) of corresponding glucose generated in 1 ml of sample solution to be evaluated, obtained by dilution with buffer/30 minutes×dilution rate [see Sakuzo FUKUI, "Biochemical Experiment Method (Method of Quantifying Reducing Sugar) 2nd edition," Gakkai Shuppan Center, pp. 23 to 24 (1990)].

Twenty-four hours after production of the slurry to be evaluated, the same measurement was carried out.

In all of Examples, there was no change in EG activity between the slurry to be evaluated immediately after addition of the enzyme and the slurry to be evaluated 24 hours after the production thereof.

[Content of Protein]

The protein contained in the slurry to be evaluated was obtained according to a burette method.

Pure water was added to bovine serum albumin, so that the content of the protein was adjusted to 5.0% by mass or less.

A burette reagent was added to the thus prepared bovine serum albumin solution in an amount that was 4 times larger than the amount of the bovine serum albumin solution, followed by fully blending. The thus obtained mixture was left under the environment of 20° C. to 25° C. for 30 minutes. Thereafter, the absorption wavelength at 540 nm was measured using a spectrophotometer. Based on the measured value, a calibration curve was drawn.

Subsequently, the slurry to be evaluated was fractionated, and a burette reagent was added to the slurry in an amount that was 4 times larger than the amount of the slurry. The thus obtained mixture was left under the environment of 20° C. to 25° C. for 30 minutes. Thereafter, the absorption wavelength at 540 nm was measured using a spectrophotometer. The measured value was written in the calibration curve, so that the amount of the protein contained in the slurry to be evaluated was obtained.

<Evaluation>

The slurries to be evaluated, which were obtained in Example 1 to 5 and Comparative Examples 1 to 5, were evaluated according to the following methods.

[Optical Properties of Cellulose-Containing Film]

The slurries to be evaluated, which were obtained in Example 1 to 5 and Comparative Examples 1 to 5, were used to form cellulose-containing films, and the haze of each cellulose-containing film was then measured. The method of forming a cellulose-containing film will be described later.

Haze was measured in accordance with JIS K 7136, using a hazemeter (manufactured by MURAKAMI COLOR RESEARCH LABORATORY Co., Ltd.; HM-150). In the evaluation results of the examples, when the haze was less than 1.0%, the result was indicated as ⊙, when it was less than 1.5%, the result was indicated as ○, when it was less than 2.0%, the result was indicated as Δ, and when it was 2.0% or more, the result was indicated as x.

Method of Forming Cellulose-Containing Film:

Ion exchange water was added to a slurry to be evaluated, so that the concentration thereof was adjusted to a solid concentration of 1.0% by mass.

Subsequently, 100 parts by mass of a water-soluble polyester resin (manufactured by GOO CHEMICAL CO., LTD.; PLASCOAT Z-221; solid concentration of 20% by mass) was added to 100 parts by mass of this ultrafine cellulose fiber-dispersed solution, so as to obtain a paint composition A.

Subsequently, a coating solution was weighed so that the finished basis weight of the obtained coating film (constituted with the solid content of the above-described paint composition A) became 50 g/m$^2$, and the coating solution was applied onto a commercially available acrylic plate, and was then dried in a constant temperature and humidity chamber at 50° C. and a relative humidity of 15%. Here, a gold frame for damming (having an inside dimension of 180 mm×180 mm) was arranged on the acrylic plate so as to have a predetermined basis weight. The coating film formed after the drying was removed from the acrylic plate, so as to obtain a coating film comprising ultrafine cellulose fibers and having a thickness of 37 μm (a cellulose-containing film).

[Mechanical Properties of Cellulose-Containing Film]

Using the cellulose-containing film obtained in the above [Optical properties of cellulose-containing film], tensile elastic modulus was measured.

The tensile elastic modulus of a test piece was measured in accordance with JIS P 8113, using a tension testing machine "Tensilon" (manufactured by A & D Company, Limited), with the exception that the length of the test piece was set at 80 nm and the distance between chucks was set at 50 mm. Upon the measurement of the ensile elastic modulus, a sample conditioned at 23° C. and at a relative humidity of 50% for 24 hours was used as a test piece, and the measurement was carried out under conditions of 23° C. and a relative humidity of 50%. In the evaluation results of the examples, when the tensile elastic modulus was 4 GPa or more, the result was indicated as ⊙, when it was 2 GPa or more, the result was indicated as ○, when it was 1 GPa or more, the result was indicated as Δ, and when it was less than 1 GPa, the result was indicated as x.

[Coating Suitability Upon Formation of Cellulose-Containing Film]

100 parts by mass of a water-soluble polyester resin (manufactured by GOO CHEMICAL CO., LTD.; PLASCOAT Z-221; solid concentration of 20% by mass) was added to 100 parts by mass of the slurry to be evaluated, which was obtained in each of Example 1 to 5 and Comparative Examples 1 to 5, so as to obtain a paint composition B. Subsequently, using a film applicator, this paint composition B was applied onto a polycarbonate film (manufactured by TEIJIN LIMITED; Panlite PC-2151; thickness: 300 μm) to form a wet film. It is to be noted that the applied width of the film applicator was set at 150 mm and the gap (applied thickness) was set at 3 mm. Sensory evaluation was carried out in terms of coating suitability upon application of the slurry to be evaluated. When unevenness was not observed upon confirmation of the wet film by visual observation, the result was indicated as ⊙, when slight unevenness was observed, the result was indicated as ○, when clear unevenness was observed, the result was indicated as Δ, and when a wet film could not be formed due to unevenness, the result was indicated as x.

TABLE 1

|  | Example 1 | Example 2 | Example 3 | Example 4 | Example 5 |
|---|---|---|---|---|---|
| Chemical treatment of ultrafine cellulose fibers | Phosphoric acid | Phosphoric acid | Phosphoric acid | Phosphoric acid | TEMPO |
| Viscosity [mPa·s] | 10000 | 750 | 6500 | 1200 | 1100 |
| Polymerization degree | 450 | 300 | 400 | 300 | 270 |
| EG activity (immediately after addition of enzyme) [U/L] | 0.084 | 840 | 0.84 | 4 | 4 |
| Content of protein [parts by mass with respect to 1 part by mass of cellulose fibers] | $3.0 \times 10^{-7}$ | $1.0 \times 10^{-3}$ | $1.0 \times 10^{-6}$ | $3.0 \times 10^{-6}$ | $3.0 \times 10^{-6}$ |
| Optical properties (film) | ○ | ○ | ○ | ⊙ | ○ |
| Mechanical properties (film) | ○ | ○ | ○ | ⊙ | ○ |
| Coating suitability | ○ | ○ | ○ | ⊙ | ⊙ |

TABLE 2

|  | Comp. Ex. 1 | Comp. Ex. 2 | Comp. Ex. 3 | Comp. Ex. 4 | Comp. Ex. 5 |
|---|---|---|---|---|---|
| Chemical treatment of ultrafine cellulose fibers | Phosphoric acid | Phosphoric acid | TEMPO | TEMPO | Phosphoric acid |
| Viscosity [mPa·s] | 16000 | 13000 | 14000 | 12000 | 600 |
| Polymerization degree | 500 | 470 | 500 | 470 | 280 |
| EG activity (immediately after addition) [U/L] | 0 | 0.002 | 0.0002 | 0.05 | 84000 |
| Content of protein [parts by mass with respect to 1 part by mass of cellulose fibers] | 0 | $7.0 \times 10^{-9}$ | $7.0 \times 10^{-9}$ | $7.0 \times 10^{-8}$ | $1.0 \times 10^{-1}$ |
| Optical properties (film) | ○ | ○ | X | X | X |
| Mechanical properties (film) | ○ | ○ | Δ | Δ | Δ |
| Coating suitability | Δ | Δ | Δ | Δ | ○ |

As is clear from Table 1, in Examples 1 to 5, in which the content of the protein and endoglucanase activity were in a favorable range, the obtained slurries to be evaluated had favorable optical properties and mechanical properties and were also excellent in terms of coating suitability, when films were formed from the slurries.

On the other hand, as is clear from Table 2, in Comparative Example 1 in which no enzymes were added, films formed from the slurries had poor coating suitability. In Comparative Examples 2 to 4, an enzyme treatment was performed on the pulp and the enzyme was then washed with ion exchange water. Even in this case, the content of the protein and endoglucanase activity were low, and coating suitability was poor. In Comparative Example 5, in which the content of the protein and endoglucanase activity were higher than a favorable range, the optical properties of the film were poor.

The invention claimed is:

1. A cellulose-containing composition comprising cellulose fibers having a fiber width of 10 nm or less and protein, wherein the protein includes an enzyme, the content of the protein is $1 \times 10^{-3}$ parts by mass or less with respect to 1 part by mass of the cellulose fibers, the polymerization degree of the cellulose fibers is 200 or more and 450 or less, and when the cellulose-containing composition having a solid concentration of 0.4% by mass is obtained, the viscosity of the cellulose-containing composition measured under conditions of 25° C. and a rotation number of 3 rpm is 10 mPa·s or more and 11000 mPa·s or less.

2. The cellulose-containing composition according to claim 1, wherein the content of the protein is $1 \times 10^{-7}$ parts by mass or more with respect to 1 part by mass of the cellulose fibers.

3. The cellulose-containing composition according to claim 1, wherein the cellulose fibers have ionic substituents.

4. The cellulose-containing composition according to claim 1, wherein the cellulose fibers have phosphoric acid groups or phosphoric acid group-derived substituents.

* * * * *